(12) United States Patent
Schutz et al.

(10) Patent No.: US 8,350,005 B2
(45) Date of Patent: Jan. 8, 2013

(54) **METHOD AND MEANS FOR ENRICHMENT REMOVAL AND DETECTION OF *LISTERIA***

(75) Inventors: Michael Schutz, Regensburg (DE); Maxi Oelschner, Regensburg (DE)

(73) Assignee: bioMérieux S.A., Marcy l'Etoile (FR)

( * ) Notice: Subject to any disclaimer, the term of this patent is extended or adjusted under 35 U.S.C. 154(b) by 416 days.

(21) Appl. No.: 12/064,317

(22) PCT Filed: Aug. 23, 2006

(86) PCT No.: PCT/DE2006/001480
§ 371 (c)(1),
(2), (4) Date: Nov. 30, 2010

(87) PCT Pub. No.: WO2007/022768
PCT Pub. Date: Mar. 1, 2007

(65) Prior Publication Data
US 2009/0136984 A1    May 28, 2009

(30) Foreign Application Priority Data
Aug. 25, 2005 (DE) .......................... 10 2005 040 347

(51) Int. Cl.
*C07K 14/195* (2006.01)
*C07H 21/00* (2006.01)
*G01N 33/53* (2006.01)

(52) U.S. Cl. .......................... 530/350; 536/23.1; 435/7.1

(58) Field of Classification Search .......................... None
See application file for complete search history.

(56) References Cited

U.S. PATENT DOCUMENTS

| | | | | |
|---|---|---|---|---|
| 5,252,466 | A | 10/1993 | Cronan | 435/69.7 |
| 5,506,121 | A | 4/1996 | Skerra et al. | 435/69.7 |
| 5,723,584 | A | 3/1998 | Schatz | 530/408 |
| 5,874,239 | A | 2/1999 | Schatz | 435/69.1 |
| 5,932,433 | A | 8/1999 | Schatz | 435/15 |
| 2004/0197833 | A1 | 10/2004 | Loessner | 435/7.2 |

FOREIGN PATENT DOCUMENTS

| | | |
|---|---|---|
| EP | 0511747 | 11/1992 |
| WO | WO 00/11472 | 3/2000 |

OTHER PUBLICATIONS

Translation of Scherer et al. (WO 00/11472, 2004).*
Jung et al., "Evaluation of Antibodies for Immunomagnetic Separation Combined with Flow Cytometry Detection of *Listeria monocytogenes*," *J. Food Prot.*, 66(7):1283-1287, 2003.
Loessner et al., "C-terminal domains of *Listeria monocytogenes* bacteriophage murein hydrolases determine specific recognition and high-affinity binding to bacterial cell wall carbohydrates," *Molecular Microbiology*, 44(2):335-349, 2002.
Loessner et al., "Heterogeneous endolysins in *Listeria monocytogenes* bacteriophages: a new class of enzymes and evidence for conserved holin genes within the siphoviral lysis cassettes," *Molecular Microbiology*, 16(6):1231-1241, 1995.
Schwarz et al., "The sodium ion translocating oxalacetate decarboxylase of *Klebsiella pneumoniae*. Sequence of the biotin-containing alpha-subunit and relationship to other biotin-containing enzymes," *Journal of Biological Chemistry*, 263:9640-9645, 1988.
Skerra and Schmidt, "Applications of a peptide ligand for streptavidin: the Strep-tag," *M. Biomolecular Engineering*, 16:79-86, 1999.
Uyttendaele et al., "The use of immuno-magnetic separation (IMS) as a tool in a sample preparation method for direct detection of *L. monocytogenes* in cheese ," *Int. J. Food Microbiol.*, 54(3):205-212, 2000.
Fluit et al., "Detection of *Listeria monocytogenes* in cheese with the magnetic immuno-polymerase chain reaction assay," *Appl. Environ. Microbiol.*, 59(5):1289-1293, 1993.
Gaeng et al., "Gene cloning and expression and secretion of *Listeria monocytogenes* Bacteriophage-Lytic Enzymes in *Lactococcus lactis*," *Applied and Environmental Microbiology*, 66(7):2951-2958, 2000.
GenBank Accession No. J03885, 1993.
International Preliminary Report on Patentability issued in International Application No. PCT/DE2006/001480, Feb. 26, 2008.
International Search Report and Written Opinion issued in International Application No. PCT/DE2006/001480, mailed Mar. 26, 2007.

* cited by examiner

*Primary Examiner* — Brian J Gangle
(74) *Attorney, Agent, or Firm* — Parker Highlander PLLC

(57) ABSTRACT

The present invention relates to polypeptide fragments of endolysin Ply511, which recognize and bind *listeria* irrespective of the serotype but which have no cell wall hydrolysing enzymatic activity. The invention further relates to methods for enrichment, removal, and detection of *listeria*.

19 Claims, 15 Drawing Sheets

*L. monocytogenes* ScottA (serovar 4b)

CBD511_f1      CBD511_f2      CBD511_f3

*L. monocytogenes* ProCC 679 (serovar 1/2a)

CBD511_f1      CBD511_f2      CBD511_f3

Fig. 8

| cfu / 25 g | 4h | | | 6 h | | | 24 h | | |
|---|---|---|---|---|---|---|---|---|---|
| | ISO | 1-step | 2-step | ISO | 1-step | 2-step | ISO | 1-step | 2-step |
| 0 | 0 | 0 | 0 | 0 | 0 | 0 | 0 | 0 | 0 |
| 2 | 0 | 0 | 0 | 0 | 0 | 0 | 0 | X | X |
| 4 | 0 | 0 | 0 | 0 | 0 | X | 0 | X | XX |
| 15 | 0 | 0 | X | 0 | X | X | 0 | XXX | XXX |
| 46 | 0 | X | X | X | X | X | X | XXX | XXX |

| cfu / 25 | 4h | | | 6 h | | |
|---|---|---|---|---|---|---|
| | ISO | 1 ml | 10 ml | ISO | 1 ml | 10 ml |
| 0 | 0 | 0 | 0 | 0 | 0 | 0 |
| 5 | 0 | 0 | 0 | 0 | 0 | X |
| 13 | 0 | X | X | 0 | X | XXX |
| 52 | 0 | X | XX | XX | XX | XXX |
| 157 | XX | XX | XXX | XX | XXX | XXX |

B

| cfu / 25 | 4h | | | 6 h | | |
|---|---|---|---|---|---|---|
| | ISO | 1 ml | 10 ml | ISO | 1 ml | 10 ml |
| 0 | 0 | 0 | 0 | 0 | 0 | 0 |
| 5 | 0 | 0 | XX | 0 | 0 | XX |
| 11 | X | 0 | X | X | X | XX |
| 45 | 0 | X | XX | XX | XX | XX |
| 135 | XX | X | XXX | XX | XX | XXX |

Fig. 13

| ply511 | ATGGTAAAATATACCGTAGAGAACAAAATTATTGCAGGATTACCTAAAGGTAAACTAAAA | 60 |
| ply511 | GGGGCTAACTTTGTTATTGCTCATGAAACTGCAAATAGCAAGTCTACTATTGACAATGAA | 120 |
| ply511 | GTAAGCTACATGACTAGGAACTGGAAGAACGCATTTGTAACTCACTTTGTAGGTGGCGGA | 180 |
| ply511 | GGTAGAGTCGTTCAGGTTGCTAATGTAAACTATGTTTCTTGGGGAGCAGGTCAGTATGCT | 240 |
| ply511 | AACTCTTATTCCTATGCGCAGGTAGAGTTGTGCCGTACAAGTAATGCAACTACATTTAAG | 300 |

| ply511 | AAAGACTATGAAGTGTACTGTCAATTACTAGTAGACCTAGCTAAAAAAGCAGGTATCCCT | 360 |
| cbd511-f1 | ---------------------------------------------AAAGCAGGTATCCCT | 15 |

| ply511 | ATTACACTTGACTCTGGTAGTAAAACTAGTGATAAAGGTATTAAATCCCATAAATGGGTT | 420 |
| cbd511-f1 | ATTACACTTGACTCTGGTAGTAAAACTAGTGATAAAGGTATTAAATCCCATAAATGGGTT | 75 |

| ply511 | GCTGATAAGCTAGGAGGAACAACACACCAAGACCCATATGCTTACTTAAGCTCATGGGGT | 480 |
| cbd511-f1 | GCTGATAAGCTAGGAGGAACAACACACCAAGACCCATATGCTTACTTAAGCTCATGGGGT | 135 |
| cbd511-f2 | -----------GGAGGAACAACACACCAAGACCCATATGCTTACTTAAGCTCATGGGGT | 48 |

| ply511 | ATTAGTAAAGCACAATTTGCTAGTGACTTGGCTAAAGTATCTGGCGGAGGAAACACAGGA | 540 |
| cbd511-f1 | ATTAGTAAAGCACAATTTGCTAGTGACTTGGCTAAAGTATCTGGCGGAGGAAACACAGGA | 195 |
| cbd511-f2 | ATTAGTAAAGCACAATTTGCTAGTGACTTGGCTAAAGTATCTGGCGGAGGAAACACAGGA | 108 |
| cbd511-f3 | -------------------GCTAGTGACTTGGCTAAAGTATCTGGCGGAGGAAACACAGGA | 42 |

| ply511 | ACAGCGCCAGCTAAACCAAGCACACCAGCACCTAAACCAAGCACACCATCTACTAACCTA | 600 |
| cbd511-f1 | ACAGCGCCAGCTAAACCAAGCACACCAGCACCTAAACCAAGCACACCATCTACTAACCTA | 255 |
| cbd511-f2 | ACAGCGCCAGCTAAACCAAGCACACCAGCACCTAAACCAAGCACACCATCTACTAACCTA | 168 |
| cbd511-f3 | ACAGCGCCAGCTAAACCAAGCACACCAGCACCTAAACCAAGCACACCATCTACTAACCTA | 102 |

| ply511 | GACAAACTTGGCTTAGTAGACTACATGAACGCTAAGAAAATGGACTCTAGCTACAGTAAC | 660 |
| cbd511-f1 | GACAAACTTGGCTTAGTAGACTACATGAACGCTAAGAAAATGGACTCTAGCTACAGTAAC | 315 |
| cbd511-f2 | GACAAACTTGGCTTAGTAGACTACATGAACGCTAAGAAAATGGACTCTAGCTACAGTAAC | 228 |
| cbd511-f3 | GACAAACTTGGCTTAGTAGACTACATGAACGCTAAGAAAATGGACTCTAGCTACAGTAAC | 162 |

| ply511 | AGAGATAAGTTAGCTAAACAGTATGGTATTGCTAACTATTCAGGAACAGCTAGCCAGAAC | 720 |
| cbd511-f1 | AGAGATAAGTTAGCTAAACAGTATGGTATTGCTAACTATTCAGGAACAGCTAGCCAGAAC | 375 |
| cbd511-f2 | AGAGATAAGTTAGCTAAACAGTATGGTATTGCTAACTATTCAGGAACAGCTAGCCAGAAC | 288 |
| cbd511-f3 | AGAGATAAGTTAGCTAAACAGTATGGTATTGCTAACTATTCAGGAACAGCTAGCCAGAAC | 222 |

| ply511 | ACTACACTCCTTAGTAAAATTAAAGGAGGAGCACCTAAACCAAGCACACCAGCACCTAAA | 780 |
| cbd511-f1 | ACTACACTCCTTAGTAAAATTAAAGGAGGAGCACCTAAACCAAGCACACCAGCACCTAAA | 435 |
| cbd511-f2 | ACTACACTCCTTAGTAAAATTAAAGGAGGAGCACCTAAACCAAGCACACCAGCACCTAAA | 348 |
| cbd511-f3 | ACTACACTCCTTAGTAAAATTAAAGGAGGAGCACCTAAACCAAGCACACCAGCACCTAAA | 282 |

| ply511 | CCTAGTACATCTACAGCTAAGAAAATTTATTTCCCACCAAATAAAGGAAACTGGTCTGTG | 840 |
| cbd511-f1 | CCTAGTACATCTACAGCTAAGAAAATTTATTTCCCACCAAATAAAGGAAACTGGTCTGTG | 495 |
| cbd511-f2 | CCTAGTACATCTACAGCTAAGAAAATTTATTTCCCACCAAATAAAGGAAACTGGTCTGTG | 408 |

Fig. 13a

```
cbd511-f3    CCTAGTACATCTACAGCTAAGAAAATTTATTTCCCACCAAATAAAGGAAACTGGTCTGTG  342 ply511       TATCCAACAAATAAAGCACCCGTTAAGGCTAATGCTATTGGTGCTATTAACCCTACTAAA  900
cbd511-f1    TATCCAACAAATAAAGCACCCGTTAAGGCTAATGCTATTGGTGCTATTAACCCTACTAAA  555
cbd511-f2    TATCCAACAAATAAAGCACCCGTTAAGGCTAATGCTATTGGTGCTATTAACCCTACTAAA  468
cbd511-f3    TATCCAACAAATAAAGCACCCGTTAAGGCTAATGCTATTGGTGCTATTAACCCTACTAAA  402 ply511       TTCGGAGGATTGACTTACACTATCCAAAAGATAGAGGAAACGGTGTATACGAAATCCAA   960
cbd511-f1    TTCGGAGGATTGACTTACACTATCCAAAAGATAGAGGAAACGGTGTATACGAAATCCAA   615
cbd511-f2    TTCGGAGGATTGACTTACACTATCCAAAAGATAGAGGAAACGGTGTATACGAAATCCAA   528
cbd511-f3    TTCGGAGGATTGACTTACACTATCCAAAAGATAGAGGAAACGGTGTATACGAAATCCAA   462 ply511       ACAGACCAATTCGGCAGAGTTCAAGTCTATGGTGCACCTAGTACAGGAGCAGTTATCAAA 1020
cbd511-f1    ACAGACCAATTCGGCAGAGTTCAAGTCTATGGTGCACCTAGTACAGGAGCAGTTATCAAA  675
cbd511-f2    ACAGACCAATTCGGCAGAGTTCAAGTCTATGGTGCACCTAGTACAGGAGCAGTTATCAAA  588
cbd511-f3    ACAGACCAATTCGGCAGAGTTCAAGTCTATGGTGCACCTAGTACAGGAGCAGTTATCAAA  522 ply511       AAATAA 1026
cbd511-f1    AAATAA  681
cbd511-f2    AAATAA  594
cbd511-f3    AAATAA  528
```

Fig. 14

```
Ply511      MVKYTVENKIIAGLPKGKLKGANFVIAHETANSKSTIDNEVSYMTRNWKNAFVTHFVGGG  60
CBD511_f1   ------------------------------------------------------------
CBD511_f2   ------------------------------------------------------------
CBD511_f3   ------------------------------------------------------------

Ply511      GRVVQVANVNYVSWGAGQYANSYSYAQVELCRTSNATTFKKDYEVYCQLLVDLAKKAGIP 120
CBD511_f1   -------------------------------------------------------KAGIP   5
CBD511_f2   ------------------------------------------------------------
CBD511_f3   ------------------------------------------------------------

Ply511      ITLDSGSKTSDKGIKSHKWVADKLGGTTHQDPYAYLSSWGISKAQFASDLAKVSGGGNTG 180
CBD511_f1   ITLDSGSKTSDKGIKSHKWVADKLGGTTHQDPYAYLSSWGISKAQFASDLAKVSGGGNTG  65
CBD511_f2   --------------------------GGTTHQDPYAYLSSWGISKAQFASDLAKVSGGGNTG  36
CBD511_f3   ---------------------------------------------ASDLAKVSGGGNTG  14

Ply511      TAPAKPSTPAPKPSTPSTNLDKLGLVDYMNAKKMDSSYSNRDKLAKQYGIANYSGTASQN 240
CBD511_f1   TAPAKPSTPAPKPSTPSTNLDKLGLVDYMNAKKMDSSYSNRDKLAKQYGIANYSGTASQN 125
CBD511_f2   TAPAKPSTPAPKPSTPSTNLDKLGLVDYMNAKKMDSSYSNRDKLAKQYGIANYSGTASQN  96
CBD511_f3   TAPAKPSTPAPKPSTPSTNLDKLGLVDYMNAKKMDSSYSNRDKLAKQYGIANYSGTASQN  74

Ply511      TTLLSKIKGGAPKPSTPAPKPSTSTAKKIYFPPNKGNWSVYPTNKAPVKANAIGAINPTK 300
CBD511_f1   TTLLSKIKGGAPKPSTPAPKPSTSTAKKIYFPPNKGNWSVYPTNKAPVKANAIGAINPTK 185
CBD511_f2   TTLLSKIKGGAPKPSTPAPKPSTSTAKKIYFPPNKGNWSVYPTNKAPVKANAIGAINPTK 156
CBD511_f3   TTLLSKIKGGAPKPSTPAPKPSTSTAKKIYFPPNKGNWSVYPTNKAPVKANAIGAINPTK 134

Ply511      FGGLTYTIQKDRGNGVYEIQTDQFGRVQVYGAPSTGAVIKK 341
CBD511_f1   FGGLTYTIQKDRGNGVYEIQTDQFGRVQVYGAPSTGAVIKK 226
CBD511_f2   FGGLTYTIQKDRGNGVYEIQTDQFGRVQVYGAPSTGAVIKK 197
CBD511_f3   FGGLTYTIQKDRGNGVYEIQTDQFGRVQVYGAPSTGAVIKK 175
```

METHOD AND MEANS FOR ENRICHMENT REMOVAL AND DETECTION OF *LISTERIA*

This application is a national phase application under 35 U.S.C. §371 of International Application No. PCT/DE2006/001480 filed Aug. 23, 2006, which claims priority to German Patent Application No. DE 10 2005 040 347.6 filed Aug. 25, 2005. The entire text of each of the above-referenced disclosures is specifically incorporated herein by reference without disclaimer.

The present invention relates to polypeptide fragments of endolysin Ply511, which recognise and bind *listeria* irrespective of the serotype but which have no cell wall hydrolysing enzymatic activity. The invention further relates to methods for enrichment, removal, and detection of *listeria*.

*Listeria* are human and animal pathogenic bacteria, which are frequently present in food, in particular in fish, meat and milk products. The genus *listeria* comprises 6 different species with 16 different serotypes. In detail, these are *L. monocytogenes* having the serotypes 1/2a, 1/2b, 1/2c, 3a, 3b, 3c, 4a, 4ab, 4b, 4c, 4d, 4e, 7; *L. innocua* having the serotypes 3, 6a, 6b, 4ab, U/S; *L. ivanovii* having the serotype 5; *L. seeligeri* having the serotypes 1/2a, 1/2b, 1/2c, 4b, 4c, 4d, 6b; *L. welshimeri* having the serotypes 1/2a, 4c, 6a, 6b, U/S, and *L. grayi* having the serotype Grayi. The two species *L. monocytogenes* and *L. ivanovii* are considered to be pathogenic. A third species, *L. seeligeri*, is regarded to be apathogenic; however, there is one case known, in which *L. seeligeri* caused meningitis in a human. The remaining species are considered to be apathogenic. About 90% of the listerioses are ascribed to *L. monocytogenes* serovar 1/2a, 1/2b, and 4b (Wing E J & Gregory S H, 2002: *Listeria monocytogenes*: Clinical and Experimental Update, J Infect Diseases 185 (Suppl 1): S18-S24).

Although only a small portion of the food related diseases is caused by *listeria* (about 1% in the USA), almost 30% of the annual fatal diseases, which are caused by food pathogens, are ascribed to this germ. Affected are above all immunosuppressed persons, e.g., elderly people, diabetics, and persons suffering from cancer and/or AIDS. Pregnant women and the unborn child represent about 25% of all cases of people diseased with invasive listerioses. Because of their ability to overcome the blood-brain barrier or the placental barrier *listeria* may cause meningitis, encephalitis, aborts, and stillbirths (Wing E J & Gregory S H, 2002, *Listeria monocytogenes*: Clinical and Experimental Update, J Infect Diseases 185 (Suppl 1): S18-S24; Doyle M E, 2001: Virulence Characteristics of *Listeria monocytogenes*, Food Research Institute, October 2001).

*Listeria* tolerate weak acids very well and are able to reproduce under relatively high salt concentrations and at temperatures from 1° C. to 45° C. The main source of infections are foods, in particular the ones which are not heat-treated prior to consumption, such as many milk products, kipper, meat products, and increasingly also ready-to-eat-products. While there is a zero tolerance for *L. monocytogenes* in ready-to-eat-foods, in many European countries, or also Canada, a contamination with *listeria* up to 100 cfu (colony forming units)/g food is allowable for certain foods. At any rate, the foods have to be tested for *listeria* contamination, however. Many of these foods, e.g., seafood, kipper, milk products or even raw vegetable ready-to-eat-products have only a limited shelf life. This frequently amounts to cost intensive product recalls, if these products are positively tested for a *listeria* contamination and a contamination beyond the allowed threshold value, respectively, after delivery. For said reason there is a great interest to significantly shorten the up to now relative long time period, which is necessary to detect a contamination.

For a sufficient control of the foods in respect to *listeria*, the detection of *L. monocytogenes* alone is not sufficient because cases of listerioses are known as well, which were caused by *L. ivanovii* and *L. seeligeri*. In addition, a testing of all *listeria* species may be used as a sanitation monitoring in connection with food production. A problem connected with the detection of *listeria* is the time, which is necessary for the detection. In particular, in food industry the detection time represents a major factor in regard to a short shelf life of some foods and a cost intensive storage, which is necessary until it has been made sure that the sample is not contaminated. Moreover, there can consistently be observed cost intensive product recalls, when contaminated goods are delivered ahead of schedule before the receipt of the control results. The standard detection times are more than 4-7 days according to ISO 11290-1:1996/FDAM 1:2004(E) and 4 to 7 days according to FDA and USDA/FSIS. For many other methods the enrichment takes up to 48 h in order to gain a sufficient amount of *listeria* for the detection without any interfering components of the food sample.

This problem was addressed by a multitude of detection methods for *listeria*, wherein many of them are also commercially available, e.g., PCR, ELISA, etc. (cf. US 2004/0197833 A1). Such a method is very promising in the case of pure cultures; however, it shows significant problems in the case of mixed cultures or complex matrices such as foods.

In this context, a method uses antibodies against the flagella proteins of *L. monocytogenes* (Skjerve, 1990; Skjerve E., Rorvik L M, Olsvik O.: Detection of *Listeria monocytogenes* in foods by immuno-magnetic separation. Appl Environ Microbiol. 1990 (11):3478-3481), which are immobilised on magnetic particles. Using a similar method in experiments with cheese (Uyttendaele et al., 2000; Uyttendaele M, Van Hoorde I, Debevere J.: The use of immuno-magnetic separation (IMS) as a tool in a sample preparation method for direct detection of *L. monocytogenes* in cheese. Int J Food Microbiol. 2000; 54(3):205-212) cell numbers of 0.5-1.5 cfu per gram cheese could be detected. However, it was found that the antibodies not only bind to the target cells. Such a method is indeed very promising in the case of pure cultures; however, it shows significant problems in the case of mixed cultures or complex matrices such as foods. Thusly, the portion of unbound non-listeria was very high. In addition, using said method sufficient *listeria* could only then be obtained, when the food homogenates were diluted, centrifuged, and enzymatically digested to enable binding of the cells to the particles. In a further experiment (Jung et al., 2003; Jung Y S, Frank J F, Brackett E R: Evalution of antibodies for immunomagnetic separation combined with flow cytometry detection of *Listeria monocytogenes*. J Food Prot. 2003; 66(7):1283-1287) Jung et al. showed that only 7%-23% of the *listeria* could be isolated from a buffer solution using the antibody coated magnetic beads.

Recovery rates of 5%-15% of the originally used *listeria* were also obtained in experiments by Fluit et al. (Fluit et al., 1993; Fluit A C, Torensma R, Visser M J, Aarsman C J, Poppelier M F, Keller B H, Klapwijk P, Verhoef J.: Detection of *Listeria monocytogenes* in cheese with the magnetic immuno-polymerase chain reaction assay. Appl Environ Microbiol. 1993; 59(5):1289-1293) with magnetic particles which were coated with monoclonal antibodies against whole *listeria* cells without flagella as well as with monoclonal antibodies against the *listeria* flagella protein. In addition, 10% of the *listeria* were not recognised by the antibodies.

A further method uses the cell binding domains (CBD) of two *listeria* phage endolysins (WO 00/11472; US2004/0197833 A1). Endolysins are phage encoded proteins, which are produced in the late phase of the phage maturation and which together with a membrane pore forming holin enables the lysis of the host cell for the release of the mature phage particles. Endolysins consist of two domains, a lytic domain and a cell binding domain (CBD). The lytic domain cleaves the peptidoglycane of the cell wall of gram positive bacteria. The CBD binds to the cell wall and determines the specificity of the endolysin.

In this method (WO 00/11472; US2004/0197833 A1) fusions of a green fluorescence protein (GFP) with the CBD (CBD118 and CBD500) of the endolysins Ply118 and Ply500 from the *listeria* phages A118 and A500 were used. These proteins were immobilised on magnetic particles and tested for their ability to enrich *listeria*. The CBD118/CBD500-system was tested with different food samples in comparison to the IDF standard method (IDF, 143A:1995). It was shown that by using the coated particles the pre-enrichment period could be significantly shortened in order to detect *listeria* in foods.

In regard to the binding properties of the CBD it was shown, however, that neither CBD118 nor CBD500 alone recognise all serotypes. Thus, it is necessary to use always a mixture with both CBD linked to particles for the enrichment, because it is not known beforehand, which serotype and which serotypes, respectively, the *listeria* represent in the samples. Thereby the amount of particles, which is to be used per food test, is duplicated resulting in an increase in cost of the system and an increase of the risk of non-listeria adhering unspecifically to the particles.

Thus, the problem underlying the present invention is to provide a method and the means to perform said method with which *listeria* of all serotypes may be detected easily and fast and be removed.

The problem is solved by the subject-matter defined in the patent claims.

The following figures illustrate the invention.

FIG. 1 schematically shows different combinations of fusion proteins with variants of the cell binding domain of the endolysin Ply511. The abbreviation A means affinity domain, "L" means linker domain, and "Z" means cell binding domain. The abbreviation His means His-Tag; the abbreviation Bio stands for a domain carrying a biotin molecule; Strep stands for STREP-TAG® (Trp-Ser-His-Pro-Gly-Phe-Lys) (SEQ ID NO:9); GFP stands for "green fluorescent protein" as a linker domain; CBD511 stands for cell binding domain of the endolysin Ply511 with the respective variants _f1, _f2, and _f3.

FIG. 2 shows fluorescence microscopic pictures of the binding of different GFP-CBD-fusions to *L. monocytogenes* ScottA (serovar 4b) and *L. monocytogenes* ProCC 679 (serovar 1/2a). For the experimental setup see experiment 1. CBD511_f1 stands for the fusion of STREP-TAG®-HisTag-GFP-CBD_f1, CBD511_f2 stands for the fusion of STREP-TAG®-HisTag-GFP-CBD_f2, and CBD511_f3 stands for the fusion of STREP-TAG®-HisTag-GFP-CBD511_f3.

FIG. 3 shows the serotype dependency of the binding of the cell binding domains CBD500 and CBD511 at different protein concentrations. Shown is the amount of the cells bound to the magnetic particles in percent (in comparison to the number) of the in toto recovered cells. The experimental setup is described in experiment 3. CBD500 stands for the fusion protein STREP-TAG®-HisTag-GFP-CBD500; CBD511 stands for the fusion protein STREP-TAG®-HisTag-GFP-CBD511_f2; ScottA (4b) stands for *L. monocytogenes* ScottA having the serotype 4b; EGDe (1/2a) stands for *L. monocytogenes* EGDe having the serotype 1/2a. The values are mean values resulting from 8 experiments. The cell number used at any time was between 75 and 120 cfu/ml.

FIG. 4 shows the dependency of the cell binding to magnetic particles on the concentration of biotinylated constructs of the CBD511-Bio-OD-CBD511_f3 (FIG. 4A) and Bio-Av-GFP-CBD511_f3 (FIG. 4B). Shown is the amount of cells bound to the magnetic particles in percent (in comparison to the number) of the in toto recovered cells. The performance of the experiment is described in experiment 4. The used cell number of *L. monocytogenes* ScottA, serovar 4b, was $1 \times 10^3$-$1 \times 10^4$ cfu/ml. The data points were determined from 2-8 independent experiments.

FIG. 5 shows the pH-dependency of the CBD511 mediated binding of *L. monocytogenes* serovar 1/2a and 4b from solutions to magnetic particles using the 2-step-method. Shown is the amount of cells bound to the magnetic particles by means of the fusion protein Bio-Av-GFP-CBD_f3 in percent (in comparison to the number) of the in toto recovered cells. The performance of the experiment is described in experiment 5. ScottA (4b) stands for *L. monocytogenes* ScottA having the serotype 4b; EGDe (1/2a) stands for *L. monocytogenes* EGDe having the serotype 1/2a. The values are mean values from 4 experiments. The cell number used at any time was between $10^3$ to $10^4$ cfu/ml.

FIG. 6 shows the salt concentration dependency of the CBD511 mediated binding of *L. monocytogenes* serovar 1/2a and 4b from solutions to magnetic particles using the 2-step-method. Shown is the amount of cells bound to the magnetic particles in percent (in comparison to the number) of the in toto recovered cells. The performance of the experiment is described in experiment 6. ScottA (4b) stands for *L. monocytogenes* ScottA having the serotype 4b; EGDe (1/2a) stands for *L. monocytogenes* EGDe having the serotype 1/2a. NaCl stands for sodium chloride. The values are mean values from 4 experiments. The cell number used at any time was about $4-8 \times 10^3$ cfu/ml.

FIG. 7 shows the dependency of the number of *listeria* cells bound to the magnetic particles on the incubation duration in case of the 1-step- and the 2-step-method. Shown is the amount of cells bound to the magnetic particles in percent (in comparison to the number) of the in toto recovered cells. The performance of the experiment is described in experiment 7. 2-step stands for 2-step-method with Bio-Av-GFP-CBD_f3 (1 μg/ml) and streptavidin coated magnetic particles (50 μg/ml); 1-step stands for 1-step-method cell binding to 300 μg/ml DYNABEADS® M-270 Epoxy covalently coated with Bio-Av-GFP-CBD_f3. The cell number used at any time was about $4-8 \times 10^3$ cfu/ml. The results represent the average of 6 experiments (2-step-method) and 2 experiments (1-step-method), respectively.

FIG. 8 shows the time dependency of the detection of *L. monocytogenes* in Camembert comparing ISO standard, 1-step-method and 2-step-method. The performance of the experiment is described in experiment 7. 5 portions camembert (25 g) were contaminated with 0, 2, 4, 15, and 46 cfu, homogenised in 225 ml Fraser ½ and incubated at 30° C. Samples were taken at the indicated time points and examined according to ISO: 11290-1:1996 FDAM 1, according to the 1-step-method and the 2-step-method. Cfu stands for colony forming units; ISO stands for performance in accordance to ISO: 11290-1:1996 FDAM 1,1-step stands for enrichment of the *listeria* using the 1-step-method using STREP-TAG®-HisTag-GFP-CBD511_12 covalently coupled to DYNABEADS® M-270 Epoxy. 2-step stands for enrichment of the *listeria* using the 2-step-method using STREP-TAG®-

HisTag-GFP-CBD511_f3 and streptavidin coated magnetic particles. The values represent the average of 2 experiments.

FIG. 9 shows the time dependency of the detection of *L. monocytogenes* in raw ham (A) and in shrimps (B) according to ISO-standard, to the Profos 2-step-method with 1 ml and to the Profos 2-step-method with 10 ml. The performance of the experiment is described in experiment 9. 5 portions a 25 g of raw ham and shrimps, respectively, were contaminated with 0, 5, 13, 52, and 157 cfu and with 0, 5, 11, 45, and 135 cfu, respectively, homogenised in 225 ml Fraser ½ and incubated at 30° C. Samples were taken at the given time points and examined according to ISO: 11290-1:1996 FDAM 1 and according to the 2-step-method with 1 ml and with 10 ml. Cfu stands for colony forming units, ISO stands for the performance according to ISO: 11290-1:1996 FDAM 1, 1 ml stands for the enrichment of *listeria* from 1 ml food homogenate in the 2-step-method with STREP-TAG®-HisTag-GFP-CBD511_f3 and streptavidin coated magnetic particles, 10 ml stands for the enrichment of *listeria* from 10 ml food homogenate in the 2-step-method with STREP-TAG®-HisTag-GFP-CBD511_f3 and streptavidin coated magnetic particles. The values represent the average of 2 experiments.

FIG. 10 shows the stripping of the *listeria* bound to the magnetic particles via the 2-step-method by alkaline buffer. Illustrated is the amount of the cells bound to the magnetic particles in percent (in comparison to the number) of the in toto recovered cells. The performance of the experiment is described in experiment 10. The *listeria* were immobilised to the magnetic particles using the 2-step-method. These *listeria*-particle-complexes were either incubated in neutral buffer (control, K) or in alkaline buffer (pH 11). After separation of the supernatant from the particles both were plated in serial dilutions on Oxford agar and incubated at 37° C. "Particle (P)" means the *listeria* cells which remained at the magnetic particles, "eluate (E)" means the *listeria* which were stripped by the respective buffer.

FIG. 11 shows the separation of the DNA-fragments after PCR using genomic DNA from *L. monocytogenes* ScottA after enrichment using the 2-step-method. The performance of the experiment is described in experiment 11. *L. monocytogenes* cells were concentrated using the 2-step-method and centrifugation, respectively, from 1 ml of *listeria* enrichment broth acc. FDA (Profos AG). On the one hand, the cells bound to the magnetic particles were stripped from the magnetic particles and the cells were cracked open with and without, respectively, Ply511 treatment using proteinase K and heat treatment (94° C.). On the other hand, the cells were cracked open at the magnetic particles with and without, respectively, Ply511 treatment using proteinase K and heat treatment (94° C.). As a control the cells were cracked open after centrifugation with and without, respectively, Ply511 treatment using proteinase K and heat treatment (94° C.). 5 µl of the cell lysates were used in a PCR, and the obtained DNA fragments were separated using agarose gel electrophoresis. "2-step" stands for the enrichment using the 2-step-method from 1 ml of *listeria* enrichment broth acc. FDA (Profos AG). Column (A) shows the break-up after stripping the bound cells off the magnetic particles using sodium phosphate pH 11 and subsequent cell lysis and release of the genomic DNA of *L. monocytogenes* ScottA. Column (B) stands for cell lysis and release of the genomic DNA of *L. monocytogenes* ScottA without stripping off the magnetic particles. Column Z (centrifugation) stands for cell lysis and release of the genomic DNA of *L. monocytogenes* ScottA after concentrating the cells using centrifugation. Ply511 stands for the cracking open the cells using the endolysin Ply511. $10^6$ and $10^5$ stands for $1.4 \times 10^6$ and $1.4 \times 10^5$ cfu/ml, respectively, in the test.

FIG. 12 shows the concentration dependency of the detection of *L. monocytogenes* (strain EGDe and ScottA) from Frankfurter sausages (FIG. 12A) and mozzarella (FIG. 12B) using the fusion proteins Bio-Av-GFP-CBD511_f3 in the 1-step- and 2-step-method. The performance of the experiment is described in experiment 12. In each case it is illustrated how many percent of the in toto used *listeria* cells of the respective strains were recovered from 1 ml samples of the foods Frankfurter sausages (FIG. 12A) and mozzarella (FIG. 12B). The values were determined from 2 experiments each.

FIGS. 13 and 13a show the comparison of the nucleic acid sequence of endolysin Ply511 (SEQ ID NO:1) with the polypeptide fragments CBD511_f1 (SEQ ID NO:3), CBD511_f2 (SEQ ID NO:5), and CBD_f3 (SEQ ID NO:7).

FIG. 14 shows the comparison of the amino acid sequence of endolysin Ply511 (SEQ ID NO:2) with the polypeptide fragments CBD511_f1 (SEQ ID NO:4), CBD511_f2 (SEQ ID NO:6), and CBD_f3 (SEQ ID NO:8).

Figure 1:
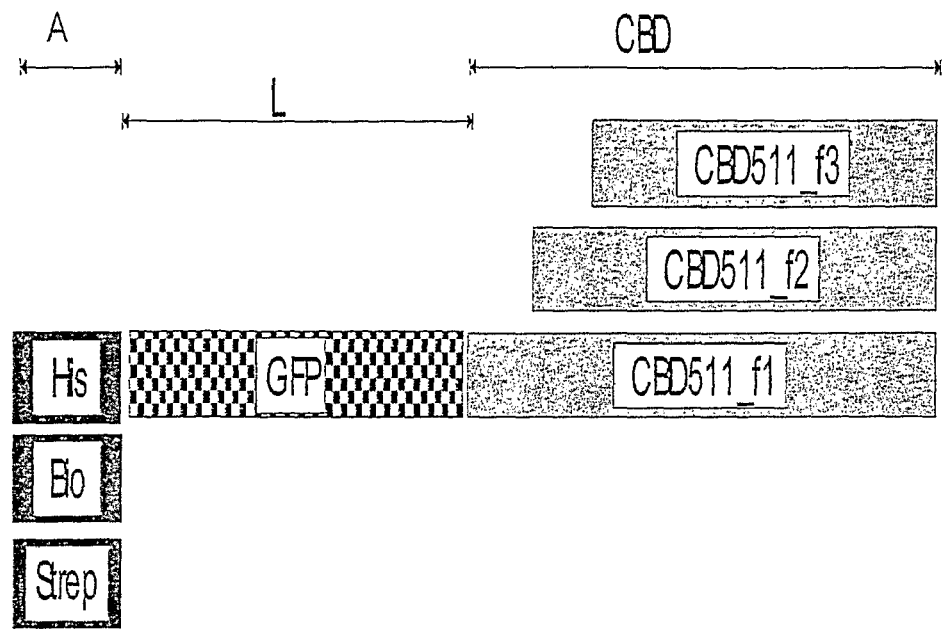
Figure 1:
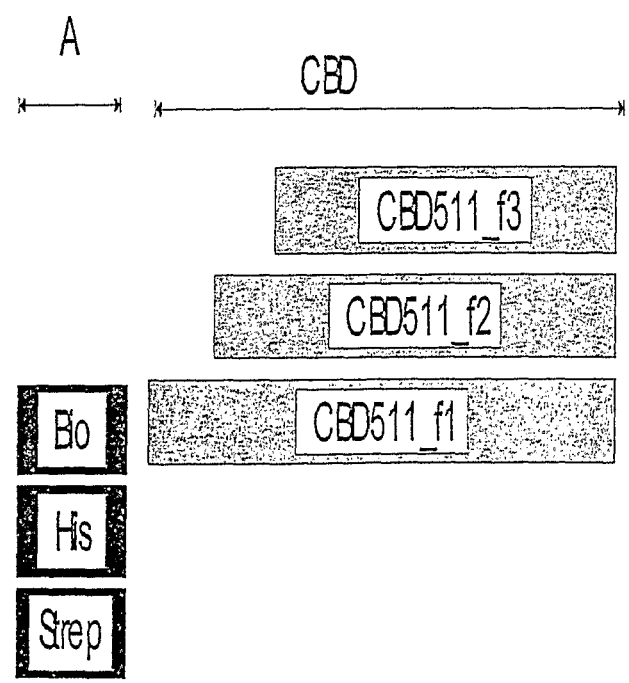
Figure 2:
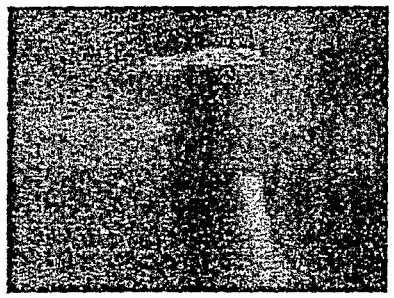
Figure 2:
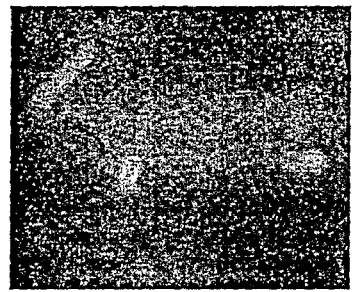
Figure 2:
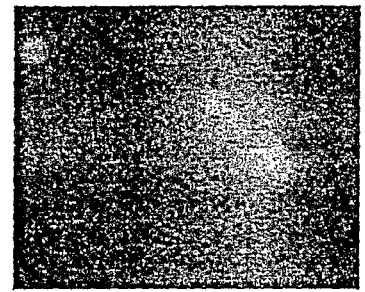
Figure 2:
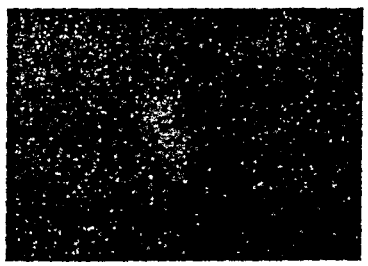
Figure 2:
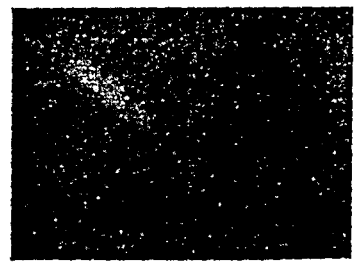
Figure 2:
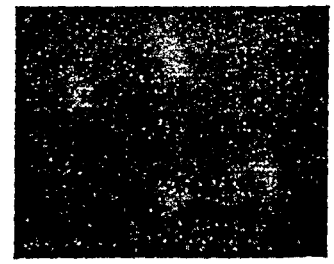
Figure 3:
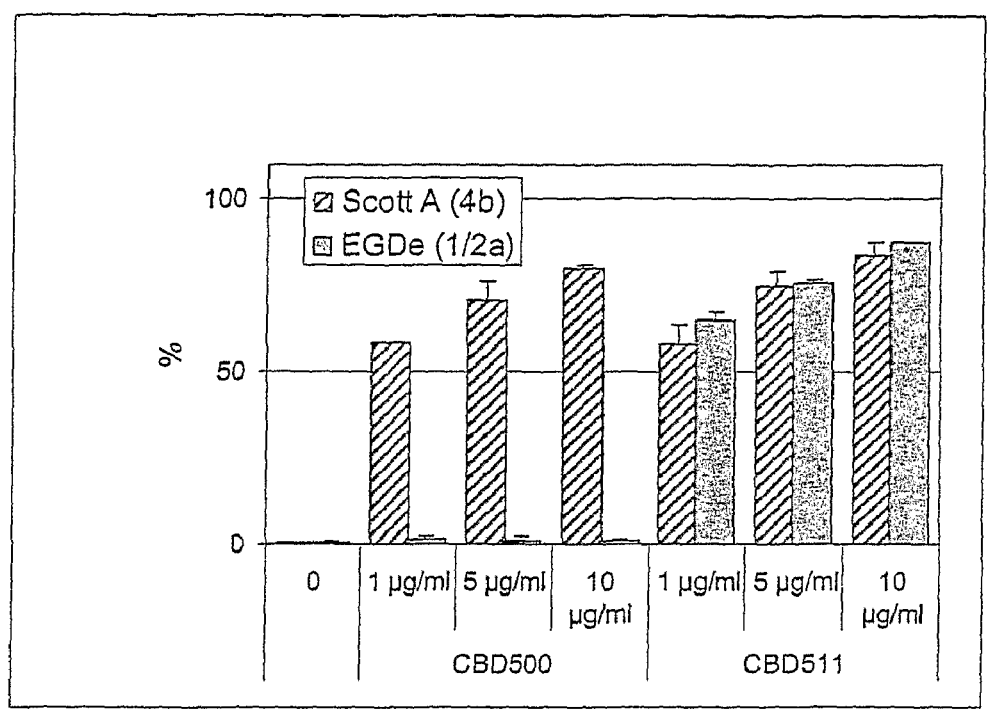
Figure 4:
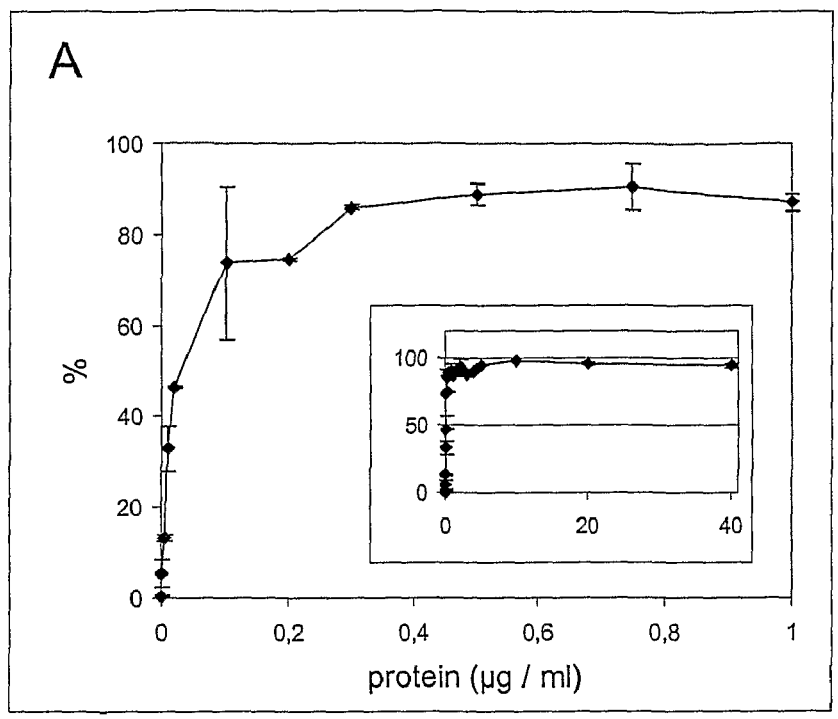
Figure 4:
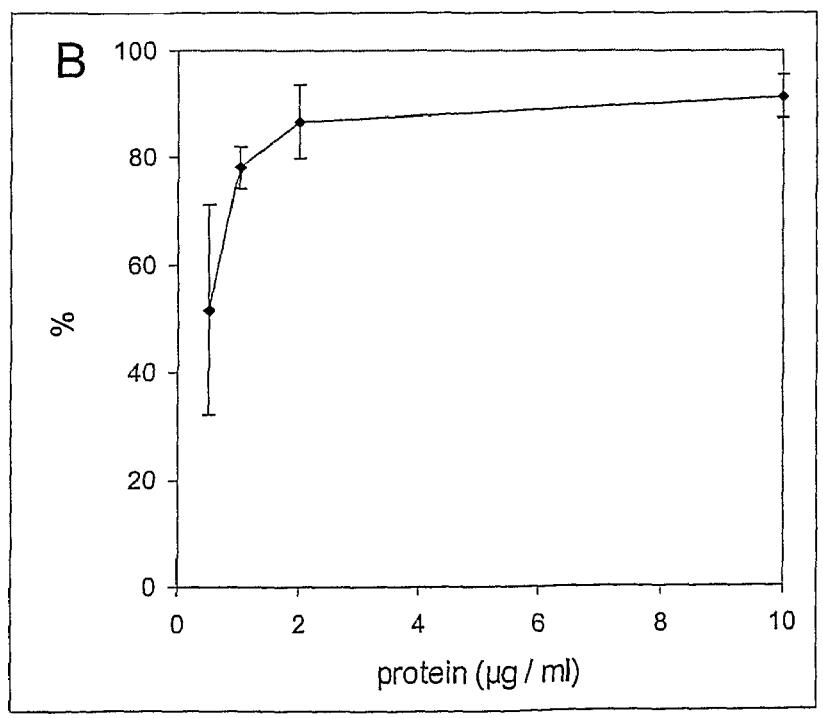
Figure 5:
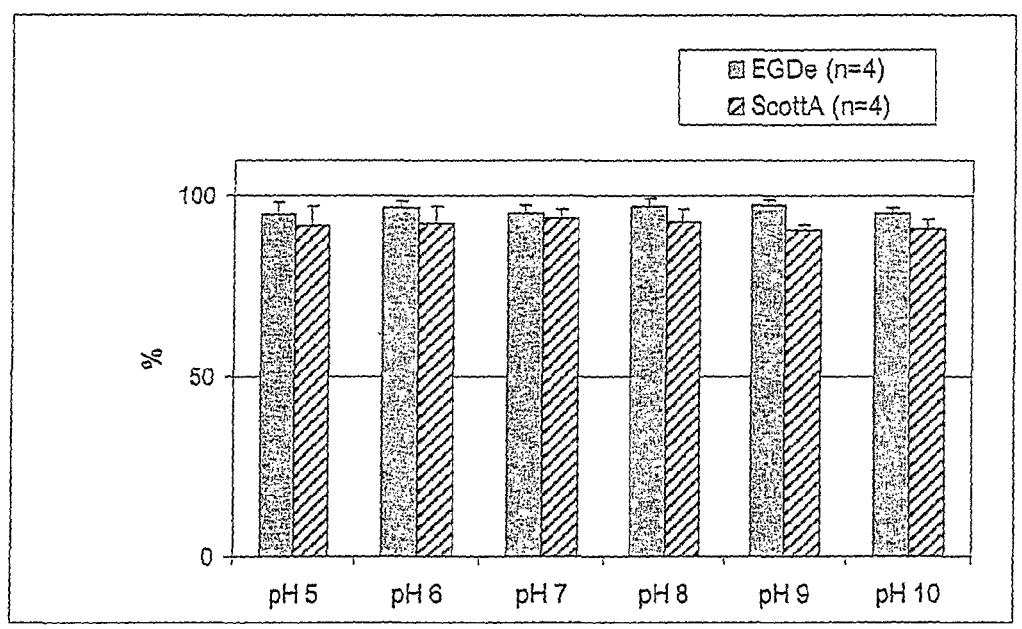
Figure 6:
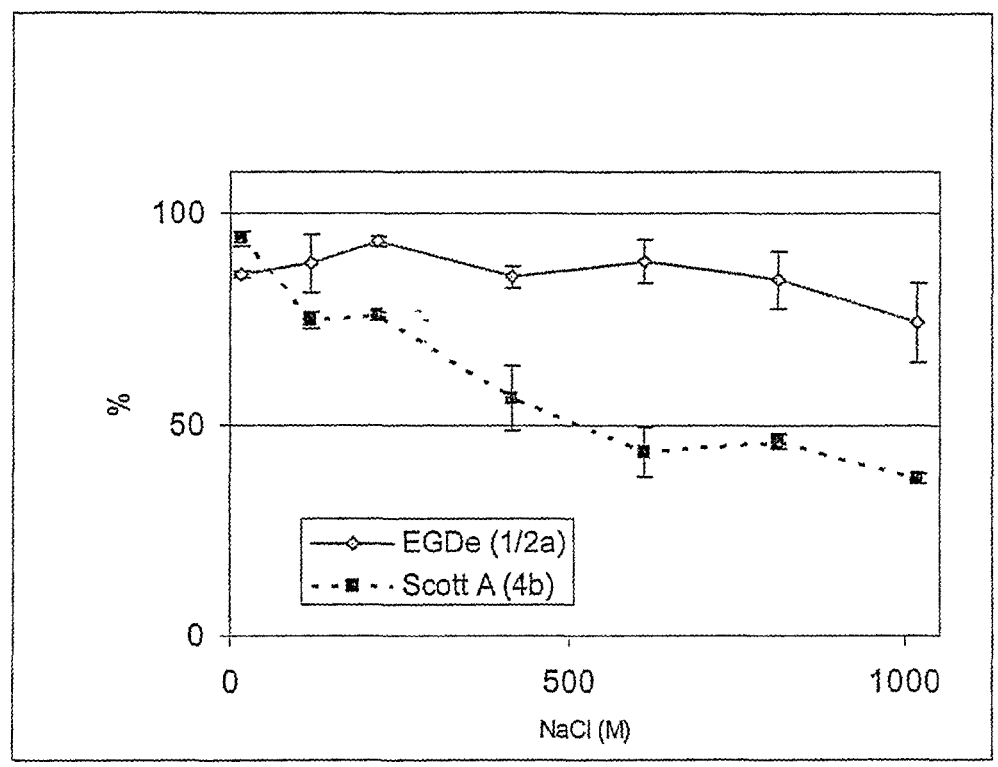
Figure 7:
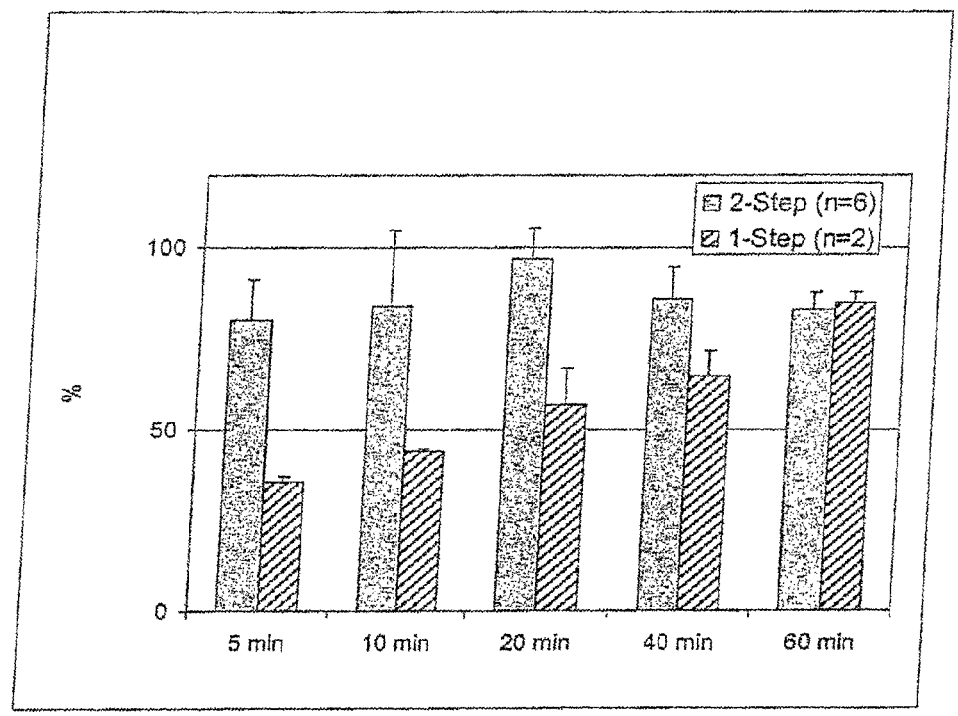
Figure 10:
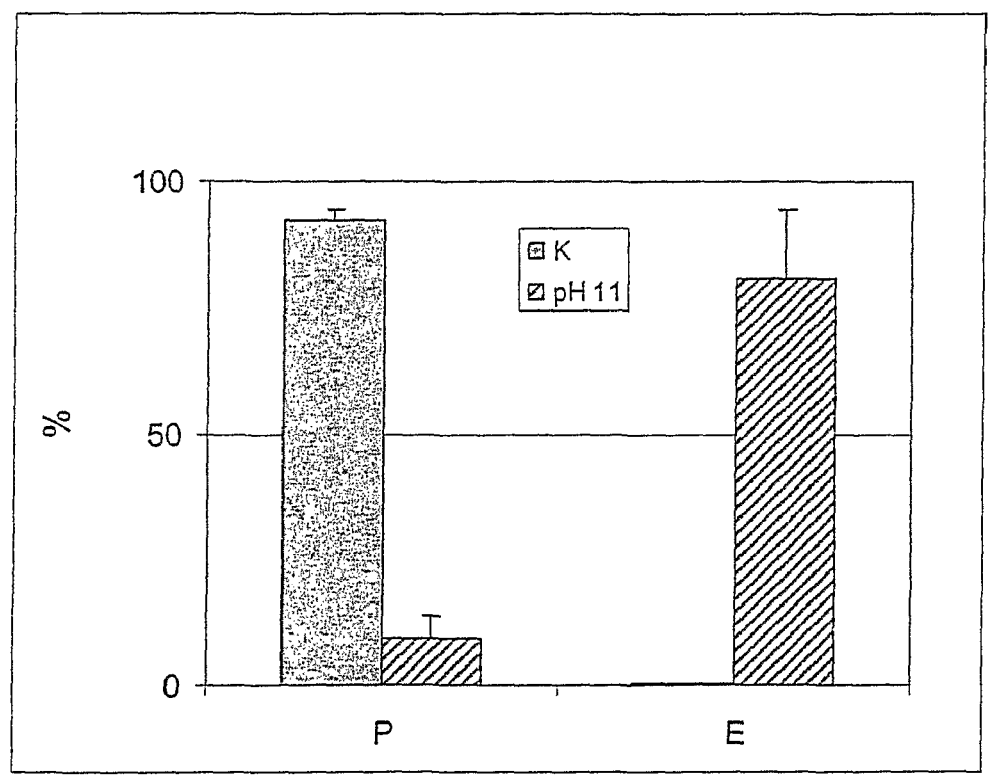
Figure 11:
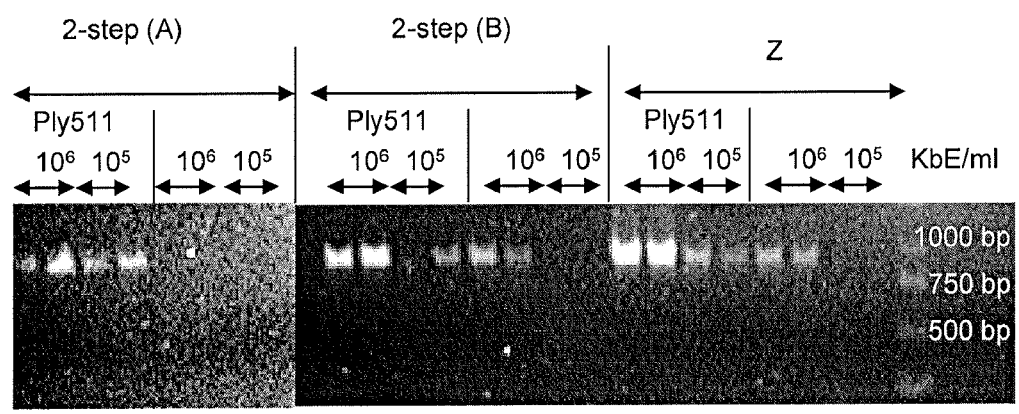
Figure 12:
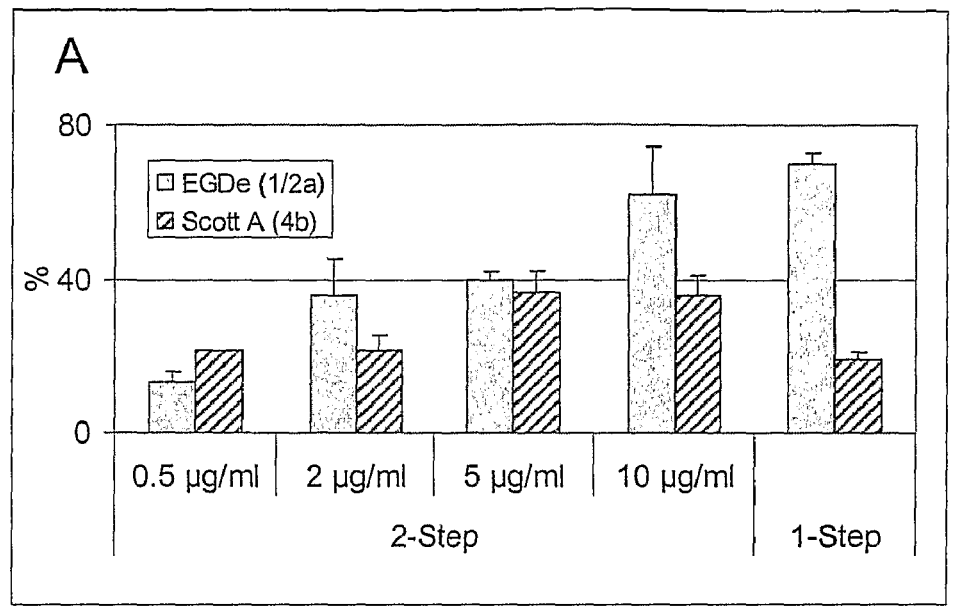
Figure 12:
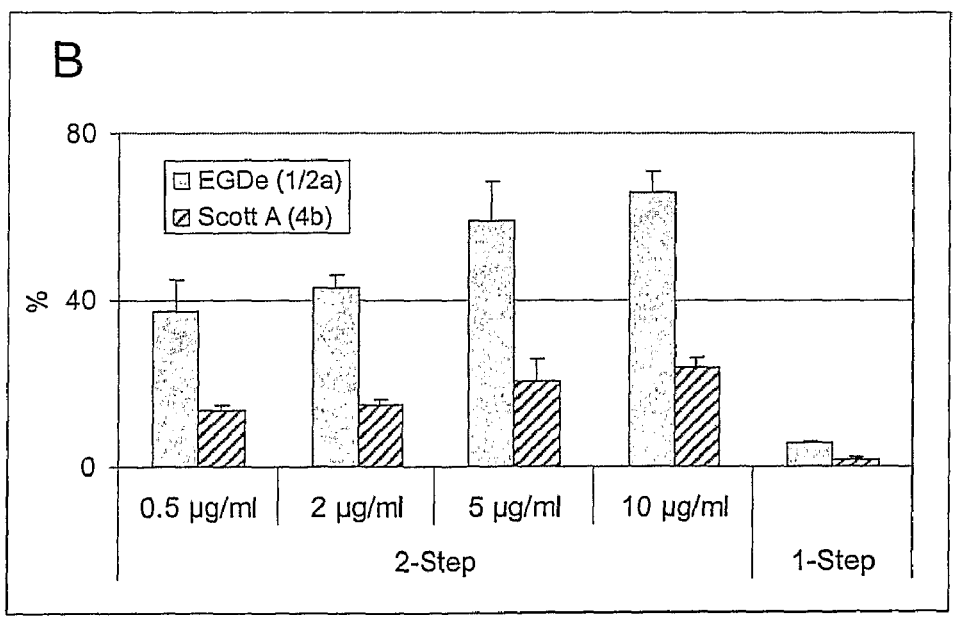

The term "*listeria*" as used herein means all bacteria, which are assigned to the genus *listeria*. In particular, the term "*listeria*" encompasses the species *L. monocytogenes* having the serotypes 1/2a, 1/2b, 1/2c, 3a, 3b, 3c, 4a, 4ab, 4b, 4c, 4d, 4e, 7; *L. innocua* having the seroptypes 3, 6a, 6b, 4ab, U/S; *L. ivanovii* having the serotype 5; *L. seeligeri* having the serotypes 1/2a, 1/2b, 1/2c, 4b, 4c, 4d, 6b; *L. welshimeri* having the serotypes 1/2a, 4c, 6a, 6b, U/S and *L. grayi* having the serotype Grayi.

The term "depletion of *listeria*" or "*listeria* removal", as used herein, means the total or partial removal of *listeria* from sample material.

The term "pre-enrichment" or "enrichment", as used herein, means the growing of *listeria* e.g., in a food sample, which was spiked with respective nutrient medium, having the aim to increase the concentration/amount of *listeria* in said sample, so that a respective detection step enables an unambiguous positive or unambiguous negative statement.

The term "sample material" or "sample", as used herein, comprises all solutions in which *listeria* are to be detected or from which *listeria* are to be removed. Exemplary for samples is the following listing: aqueous solution and mixtures of water and organic solvents, food, media, blood, blood products, plasma, serum, urine, protein solutions, water-ethanol-mixtures. Furthermore, comprised are also solutions in which non-aqueous, solid substances were solved, which are to be examined or to be isolated, for example protein, DNA, RNA, sugars, salts, food, food-media-homogenates, medicaments, vaccines, organic and inorganic chemicals (e.g., NaCl, $MgCl_2$, purines, pyrimidines, etc.).

The term "endolysin", as used herein, relates to a naturally phage encoded enzyme which serves for the release of new phages at the end of a respective phage reproduction cycle. These endolysins consist of an enzymatic active domain and a domain binding to the cell wall of the respective host cell. In addition, said term is understood to comprise also the similarly composed autolysins. These are bacteria encoded and consist also of an enzymatic active cell wall hydrolysing domain and a domain binding to the cell wall of the target bacterium.

The term "CBD", as used herein, relates to polypeptide fragments, wherein the respective amino acid sequence corresponds to a portion in endolysins. Said portion is responsible for the binding of the endolysins to the *listeria* cell wall. Said polypeptide fragments are not enzymatically active. The CBD may also be present as a gene fusion with a spacer molecule (GFP, MBP, biotinylation domains) with and without an affinity tag (His-Tag, Strep-Tag, Avi-Tag, biotinylation domains) or also as a gene fusion only with affinity tag (His-Tag, STREP-TAG®, Avi-Tag, biotinylation domains).

The term "unspecific immobilisation" or "undirected immobilisation", as used herein, means that the coupling of a CBD to a matrix is achieved via amino acid residues (e.g., primary amines), which are dispersed over the entire polypeptide surface. The selection of the residue, which is used for the coupling of the single polypeptide molecule, is performed randomly. In this case the CBD may either be coupled directly to activated groups on a matrix (e.g., binding to DYNABEADS® M-270 Epoxy, Dynale), or a group may be chemically introduced into the CBD (e.g., introduction of biotin with EZ-link-sulfo-NHS-LC-LC-Biotin, Pierce), and via said group the CBD may be bound to a matrix, which is coated with a ligand for the introduced group (e.g., streptavidin). The term "directed immobilisation", as used herein, means that the coupling of a CBD is performed via amino acid residues or other residues (e.g., glycosylations of the protein) whose position in the protein (e.g., N- or C-terminal) is known. The selection of these groups for coupling is performed by the selection of suitable reaction partners/linkers, which react preferably with said residues (e.g., coupling of sulfhydryl residues to iodoacetate residues; iodoacetate reacts a thousand times faster with sulfhydryl residues than with amino residues). The term means moreover that the nucleotide sequence of the CBD is fused with the nucleotide sequence of an affinity tag (e.g., STREP-TAG® or His-Tag), which binds to a specific matrix (e.g., streptavidin coated magnetic particles or nickel-chelate-ligands). Said term means moreover that the nucleotide sequence of the CBD is fused to the nucleotide sequence of a polypeptide, which is recognised by other proteins, in which said other proteins introduce a molecule at a defined position (e.g., Avi-Tag or the biotinylation domain of oxalacetate decarboxylase of *Klebsiella*).

The term "surface" or "carrier", as used herein, comprises all materials to which a coupling or adhesion of a CBD-molecule is possible, such a glass surfaces, chromatography materials, e.g., agarose or sepharose, plastic surfaces, e.g., polystyrene or polypropylene, filter materials, e.g., cellulose.

The term "1-step-method", as used herein, relates to a method in which the CBD were either directedly or undirectedly immobilised to a suitable carrier or surface already prior to the addition of a sample. After incubation of the immobilised CBD with the sample the *listeria* CBD-carrier-complex is removed from the sample and subsequently optionally washed.

The term "2-step-method", as used herein, relates to a method in which suitable non-immobilised CBD are brought into contact and incubated with the sample. The formed *listeria*-CBD-complexes are subsequently brought into contact with a suitable carrier or a surface so that the *listeria*-CBD-complexes are bound to the carriers or surfaces via CBD. Subsequently, the *listeria*-CBD-carrier-complexes are removed from the sample and optionally washed. Suitable CBD are modified with a polypeptide or a chemical group in such a way that they specifically bind to a carrier or a surface, which are coated with the respective binding partner of the polypeptide or the chemical group.

The present invention relates to polypeptide fragments, which are derived from the endolysin Ply511 of the phage A511 and are responsible for the binding of the phage to the cell wall of *listeria*. The amino acid sequence of the full-length endolysin Ply511 is depicted in SEQ ID NO:2 and the nucleic acid sequence coding therefore is depicted in SEQ ID NO:1. Surprisingly, the isolated polypeptide fragments of the endolysin Ply511 according to the invention exhibit a binding spectrum, which deviates from the lysis spectrum of the full-length endolysin Ply511. Whereas the endolysin Ply511 hydrolyses also at least a portion of the genus *bacillus* besides all serotypes of *listeria*, exclusively *listeria* are recognised and bound by the isolated polypeptide fragments according to the invention.

The present invention relates to polypeptide fragments of the endolysin Ply511 having the property to bind to the cell wall of *listeria*, wherein the polypeptide fragments do not exhibit any enzymatically active cell wall hydrolysing regions anymore. Furthermore, the invention relates to the nucleic acid sequences coding for the polypeptide fragments according to the invention. The polypeptide fragments according to the invention are referred to in the following also as "cell wall binding domains" (CBD). The CBD recognise and bind all *listeria* irrespective of their serotype, however, in addition, they do not recognise and bind any other species.

Preferably, the polypeptide fragments according to the invention exhibit an amino acid sequence (referring to the full-length sequence according to SEQ ID NO:2) at least from position 116 to 341 and at the most from 180 to 341. The polypeptide fragments according to the invention hence correspond at the N-terminal end to any position in the range from position 116 to position 180 and at the C-terminal end to the position 341. The range from position 116 to 180 is not exactly fixed on this region but may be shifted by a few amino acid positions in the direction to the N- or C-terminus as long as the polypeptide fragments do not exhibit any cell wall hydrolysing activity and the cell wall binding activity is sustained. Preferably, the invention relates furthermore to nucleic acid molecules encoding the described preferred polypeptide fragments.

The present invention relates furthermore to modified polypeptide fragments and the nucleic acid sequences coding for the modified polypeptide fragments according to the invention.

Especially the CBD may be coupled to low molecular substances, e.g., biotin. It may be chemically introduced into the CBD or by fusion of the CBD with a polypeptide, in which biotin is introduced in vivo or in vitro using another protein. Such polypeptides are, e.g., biotinylation domains, i.e., regions in naturally occurring polypeptides, which are biotinylated. Such biotinylation domains are exhibited, e.g., by the oxalacetate decarboxylase of *Klebsiella* (U.S. Pat. No. 5,252, 466 and EP 0511747), the *Salmonella typhimurium* oxalacetate decarboxylase, the *Propionibacterium* shermanii transcarboxylase subunit, the biotin carboxyl carrier protein of the *Escherichia coli* acetyl-CoA carboxylase, the *Saccharomyces cerevisiae* pyruvate carboxylase or the *Saccharomyces cerevisiae* acetyl-CoA carboxylase. Such a polypeptide may, however, also be the Avi-Tag (avidity-patents U.S. Pat. No. 5,932,433, U.S. Pat. No. 5,874,239, and U.S. Pat. No. 5,723, 584). Furthermore, a biotin may be chemically specifically coupled to a group by fusion with a polypeptide which carries said group, which is not or seldom—but hardly accessible—present in the protein (e.g., cysteine). Furthermore, instead of biotin, the so-called STREP-TAG® (Skerra, A. & Schmidt, T. G. M. Biomolecular Engineering 16 (1999), 79-86, U.S. Pat. No. 5,506,121) may be used, which is a short amino acid sequence and binds to streptavidin. Furthermore, the His-Tag may be used. It is also possible to combine different tags and in such a way to use the different binding affinities of the different tags, e.g., STREP-TAG® and His-Tag, or biotinylation domain and His-Tag. The biotinylation domains as well as the Avi-Tag, the STREP-TAG® as well as the His-Tag are preferably coupled to the CBD using DNA-recombination technology. Preferably, the fusion protein consists of the biotinylation domain of the oxalacetate decarboxylase from *Klebsiella* or the Avi-Tag, the STREP-TAG® or the His-Tag, which are bound to the N-terminal end of the CBD at their C-terminal end. Such a fusion, however, may also be one of the above-mentioned tags, with whose C-terminal end the N-terminus of another protein, which is used as a kind of "spacer molecule", is coupled, e.g., GFP or maltose binding protein. In this case, the CBD may be coupled via its N-terminal end to the C-terminal end of said other protein.

However, the biotinylation domains may also act as "spacer molecule" such as GFP or MBP, because they are bigger than the other mentioned tags such as His-Tag, STREP-TAG®, or Avi-Tag. They may kind of fulfil a double function. Since CBD represent fragments from larger proteins, they are usually relatively small (about 100 to 300 amino acids). Thus, it may be sensible or necessary to introduce a kind of spacer between the CBD domain and the group, which is responsible for the immobilisation on the carrier. This may prevent, on the one hand, that the CBD is denatured by the immobilisation, which is associated with the loss of its binding activity to the bacterial surface; on the other hand, the accessibility of the bacteria to the CBD may be improved as well as unspecific binding to the surfaces reduced, if the CBD are in a distance from the surfaces. Furthermore, the spacers may contribute to the fact that the groups, which are responsible for the immobilisation to the surfaces, are more accessible if they are not directly fused to the CBD.

The above-mentioned coupling may be performed directedly, e.g., at the N- or C-terminus, or undirectedly. The directed coupling is performed using a suitable, reactive amino acid, which in CBD does not frequently occur as a surface exposed amino acid such as cysteine, which was specifically introduced at a suitable position. Preferably, the coupling may be also performed in a direct way by using other amino acids, or, as it is also the case with cysteine, by using a "spacer" or "cross linker" (monofunctional or bifunctional) in an indirect way.

In case of the cysteine coupling all bifunctional cross linkers having NH— and SH-reactive groups are possible, with or without intermediate spacers, e.g., 11-maleimidoundecanoic acid sulfo-NHS or succinimidyl-4-[N-maleimidomethyl]-cyclohexane-1-carboxy-[6-amido]caproate. In the case that no spacers are present 8-12 C-atom-spacers having a terminal NH-group may be introduced. Preferably, the cysteine coupling is performed using a specific biotinylation of the cysteine using, e.g., EZ-link-PEO-maleimide activated biotin (Pierce).

The polypeptide fragments according to the invention may be used for the methods for enrichment, removal, and detection of *listeria* as described hereinafter.

The present invention relates to a method for the enrichment of *listeria* from a sample (so-called 1-step-method), the method comprising the following steps:

a) incubating or contacting a sample with a CBD, which is unspecifically or directedly immobilised to a solid carrier b) separating the carrier-CBD-listeria-complex from the sample, and c) optionally washing away of sample components unspecifically adhering to the carrier-CBD-*listeria*-complex.

For the enrichment method according to the invention the CBD, which is the polypeptide according to the invention, are coupled to solid carriers. The solid carriers may be magnetic or non-magnetic particles as well as filling materials for chromatography columns (e.g., sepharose materials), cellulose, filtration media, glass particles, centrifugation or sedimentation materials (e.g., agarose particles).

The coupling of the polypeptide according to the invention, in the following referred to also as CBD, may be performed unspecifically, or it can be preferentially performed in a directed manner, via, e.g., a selective biotinylation, or coupled using a spacer or a linker. The CBD may be unspecifically bound to chemically activated solid phases, e.g., solid phases with epoxy groups, tosyl- or NHS-groups using a reaction with amino acid side chains of the CBD. The accessibility of the CBD for *listeria* may be increased for example by the fact that the CBD is present in a protein fusion with a polypeptide chain which exhibits a higher affinity to specific activated surfaces than the CBD (e.g., GFP on activated polystyrene). In particular, the polypeptide according to the invention may exhibit the above described properties and modifications.

The enrichment of the *listeria* may be performed using a magnetism based method or using chromatographic methods or using the so-called "batch" method.

The duration of the incubation of the sample with the respective carrier material coupled to CBD has to be adapted to the respective sample and may vary between 1 min and 24 h, in particular, for about 5-60 min or about 30-180 min or even over night if needed.

If the CBD coated carrier material consists of magnetic particles the sample is incubated with the carrier material. Subsequently, the carrier-CBD-listeria-complex is magnetically separated form the sample by applying a magnetic field. In case of the batch-method the *listeria* contaminated sample is mixed with the carrier material, to which the CBD according to the invention is covalently coupled, and incubated together. Subsequently, the carrier-CBD-listeria-complex may be centrifuged or sedimented away from the sample or be filled onto a column and eluted or filtrated away. The enrichment using the batch-method, i.e., with pre-incubation of sample and with the respective CBD-coupled carrier materials, may be sensible especially in the case of very low *listeria* concentrations.

The enrichment of *listeria* using chromatography columns may be performed also in a pure flow through method, however. For this purpose firstly the CBD loaded carrier material is put onto a chromatography column. The *listeria*-contaminated sample is applied to said column and flows through it, whereby the *listeria* bind to the CBD and remain on the column. The sample itself does ideally not show any interaction with chromatography material and may be found in the flow through. The flow rate is dependent on the volume and geometry of the column. Furthermore, the flow rate is dependent on the volume and the amount of *listeria* in the sample, in order to achieve an efficient depletion even in the case of low *listeria* concentrations by a long as possible contact time between column and *listeria*. In this context the contact time is the time, which is needed by the sample from applying it onto the column until its outflow. The *listeria* bound to the column may be removed from the column again by washing with suitable buffers, so that the columns may be repeatedly reused.

The present invention relates furthermore to a method for the enrichment of *listeria* from a sample (so-called 2-step-method), the method comprising the following steps:

a) incubating or contacting a sample with CBD, which is fused to a polypeptide or modified with a chemical group, so that it binds specifically to a carrier, which is coated with the respective binding partner of the polypeptide or the chemical group b) contacting and incubating the *listeria*-CBD-complex with a carrier which is coated with the respective binding partner of the polypeptide or the chemical group c) separating the carrier-CBD-listeria-complex from the sample, and d) optionally washing away of sample components unspecifically adhering to the carrier-CBD-*listeria*-complex.

In particular, the polypeptide according to the invention, hereinafter also referred to as CBD, may exhibit the above described properties and modifications.

The coupling of the CBD to another protein, by which the biotin is introduced, may be performed directedly, e.g., at the N- or C-terminus, or may be performed undirectedly. The directed coupling is performed using a suitable, reactive amino acid, which in CBD does not frequently occur as a surface exposed amino acid such as cysteine, which was specifically introduced at a suitable position. Preferably, the coupling may be also performed in a direct way using other amino acids, or, as it is the case with cysteine, using a "spacer" or "cross linker" (monofunctional or bifunctional) in an indirect way.

In case of the cysteine coupling all bifunctional cross linkers having NH— and SH-reactive groups are possible, with or without intermediate spacers, e.g., 11-maleimidoundecanoic acid sulfo-NHS or succinimidyl-4-[N-maleimidomethyl]-cyclohexane-1-carboxy-[6-amido]caproate. In the case that no spacers are present 8-12 C-atom-spacers having a terminal NH-group may be introduced. Preferably, the cysteine coupling is performed using a specific biotinylation of the cysteine using, e.g., EZ-link-PEO-maleimide activated biotin (Pierce). Furthermore, the coupling may be performed using known coupling reactions to protein residues such as for example carboxyl, amino, hydroxyl, or sulfhydryl residues.

The duration of the incubation and the separation of the carrier-CBD-listeria-complex are performed as for the above described 1-step-method.

The methods according to the invention are not only suitable for the enrichment but also for the removal of *listeria* from a sample.

Furthermore, the present invention relates to a method for the detection of *listeria* in a sample. The *listeria* detection comprises further steps following the above described method steps for enrichment, wherein the following detections may be performed both with the 1-step-method and with the 2-step-method.

For example the following detections may be used: detection of the *listeria* in the carrier-CBD-*listeria*-complex or after stripping them off the carrier material, using selective growth conditions, e.g., plating and incubation on selective media plates; detection of the target cell DNA, e.g., using PCR or DNA hybridisation methods; detection of the target cell cell wall or components thereof, e.g., using cell binding domains of endolysins or antibodies; detection of target cell components, e.g., proteins, using ELISA or enzymes via their activity, or of, e.g., ATP; detection using a target cell specific bacteriophage, e.g., A511-luxA. Preferably, the detection of the target cell DNA is performed, e.g., using PCR or the detection of target cell components, e.g., of proteins, is performed using ELISA after cracking the *listeria* open using a *listeria*-specific endolysin, e.g., Ply511.

Furthermore, the detection of the *listeria* in the carrier-CBD-listeria-complex or after stripping them off the carrier material may be performed using a further CBD, which is coupled to an enzymatically active polypeptide, so that the reaction product may be detected using the enzymatic reaction. Further, the additional CBD may be fused to a fluorescent protein and with a tag (e.g., STREP-TAG®-HisTag-GFP-CBD), which is subsequently bound by a conjugate of an enzyme and a protein, which binds specifically to the tag (e.g., streptavidin-alkaline phosphatase conjugate).

The methods according to the invention are characterised by the following advantages:

- Only a single binding molecule, namely the CBD according to the invention, is necessary to recognise and to bind all *listeria* in a serotype independent way.
- A significantly lower amount of CBD is required per method. Since it is not known for a sample to be examined which *listeria* of which serovar group are present in the sample, a significantly greater amount in terms of amount has to be used when working with the binding molecules of the state of the art, for example CBD118 or with CBD500, in order to be sufficiently sensitive for all serovar groups. In contrast, the CBD according to the invention—which bind all serovar types of *listeria*—are equally sensitive although applied in a lower polypeptide amount.
- Thus, less carrier material is required, e.g., magnetic particles. Carriers are always a source of possible disturbing factors, e.g., for subsequent detection methods. In this context, bacteria or other sample components, which bind unspecifically to the respective carrier, may lead to false results. In addition, the carrier is a decisive cost factor.
- Although exhibiting the same incubation time the present invention enables a quicker enrichment of the target germs, thus resulting in a saving of time.
- In case of the so-called 2-step-method binding molecules for different germs may be applied at the same time, e.g., for *listeria* and *salmonella*, and be enriched from the sample with the same carrier (e.g., streptavidin coated magnetic particles). Subsequently, the individual species and/or serotypes may be determined using a subsequent specific detection.

Furthermore, the present invention relates to a kit, comprising a carrier immobilised with the polypeptide fragments according to the invention as well as the buffer solutions, e.g., washing buffer, stripping buffer, and/or cell cracking buffer, required for the enrichment and the detection of the *listeria*. Furthermore, the present invention relates to a kit, comprising a modified polypeptide fragment according to the invention, a carrier immobilised with the respective binding partner of the modification of the polypeptide fragment as well as the buffer solutions, e.g., washing buffer, stripping buffer, and/or cell cracking buffer, required for the enrichment and the detection of the *listeria*.

The following examples illustrate the invention and are not to be considered to be limiting. Unless otherwise indicated, molecular biological standard methods were used, such as described for example in Sambrook et al., (1989): Molecular cloning: A Laboratory Manual $2^{nd}$ edition, Cold Spring Harbor Laboratory Press, Cold Spring Harbor, N.Y.

Experiment 1

Detection of the Binding of CBD511 Fusions Having Different Lengths to *Listeria*

The different CBD511 fusion proteins STREP-TAG®-HisTag-GFP-CBD511_f1, STREP-TAG®-HisTag-GFP-CBD511_f2 and STREP-TAG®-HisTag-GFP-CBD511_f3—heterologously expressed in *E. coli* HMS174 (DE3)—were purified using Ni-affinity chromatography (Qiagen) following the instructions of the manufacturer of the column chromatography material. 50 μl of an overnight culture of *Listeria monocytogenes* ScottA (serovar 4b) or *Listeria monocytogenes* ProCC679 (serovar 1/2a) were mixed with about 2 μg of the purified protein and incubated for 2 min at RT. After addition of 1 ml of PBST (10 mM sodium phosphate pH 8, 150 mM NaCl, 0.05% Tween 20) the cells were centrifuged, 2× washed in 0.5 ml and resuspended in 50 ml of PBST. The binding was controlled under the fluorescence microscope. It was shown that the HisTag-GFP-CBD-variants bind both *listeria* serotypes 4b and 1/2a.

Experiment 2

Genus Specific Binding of the STREP-TAG®-GFP-CBD511

The *listeria* were grown overnight in 2 ml of *listeria* enrichment broth acc. FDA (Profos AG) at 30 or 37° C., *Bacillus, Chryseobacterium, Citrobacter, Escherichia, Enterobacter, Klebsiella, Cocuria, Pseudomonas, Salmonella, Stenotrophomonas*, and *Yersinia* were grown in Lauria-Bertani bouillon (Profos AG) at 30 or 37° C. *Campylobacter* was grown in *Campylobacter* enrichment bouillon (Profos AG) under semi-aerobic atmosphere (CampyGen-Oxoid) at 42° C., *Clostridium* was grown in TYG medium at 42° C. under anaerobic atmosphere (Genbox anaer, Biomerieux). *Lactobacillus* was cultivated at 37° C. in MRS-bouillon (Profos AG), *Staphylococcus* was cultivated in BHI bouillon (Profos AG). The cells were centrifuged, 1× washed in 1 ml of TBST (10 mM TrisHCl, pH 8, 150 mM NaCl, 0.05% Tween 20), resuspended in 200 µl of PBST and heat inactivated for 15 min at 80° C.

a) NC Test

Examination of the binding of the fusion proteins to immobilised *listeria* cells:

About 20-30 µl of these suspensions were spotted on a nitrocellulose membrane (Sartorius AG) and baked for 30 min at 80° C. After wetting with TBST the membrane was blocked for 30 min in BSA solution (1% w/v in TBST) and incubated with STREP-TAG®-HisTag-GFP-CBD511_f2, STREP-TAG®-HisTag-GFP-CBD500 or STREP-TAG®-HisTag-GFP-CBD118 (10 µg/ml each) at RT under gentle agitation for 30 min. Subsequently, the membrane was washed 2×15 min in TBST and incubated for 30 min with streptaktin-AP-conjugate (IBA) in TBST. After washing (4×15 min TBST) the membrane was incubated in staining solution (100 mM TrisHCl pH 9.5, 100 mM NaCl, 5 mM $MgCl_2$, 0.18 mg/ml NBT (Applichem) and 0.22 mg/ml BCIP (Applichem)) for about 15-30 min. The reaction solution was removed, the membrane washed in water and dried.

Table 1 shows the result of binding of the cell binding domain CBD511 to non-listeria.

| Species | Strain Profos Culture Collection (ProCC) | alternative strain description | Binding of CBD511 |
|---|---|---|---|
| Bacillus cereus | 332 | | no |
| Bacillus mycoides | 328 | | no |
| Bacillus sp. | 534 | | no |
| Bacillus thuringiensis | 19 | | no |
| Bacillus thuringiensis | 471 | CC5 | no |
| Bacillus vallismortis | 20 | | no |
| Bacillus subtilis | 310 | | no |
| Campylobacter lari | 986 | | no |
| Campylobacter jejuni | 851 | NC12662-02 | no |
| Clostridium perfringens | 780 | NCTC 3110 | no |
| Clostridium perfringens | 1029 | | no |
| Clostridium perfringens | 1030 | | no |
| Clostridium sordelli | 1039 | | no |
| Chryseobacterium meningosepticum | 333 | | no |
| Chryseobacterium sp. | 337 | | no |
| Citrobacter amalonaticus | 367 | DSMZ 4593 | no |
| Citrobacter freundii | 352 | | no |
| Citrobacter freundii | 249 | | no |
| Enterobacter aerogenes | 205 | DSMZ 30053 | no |
| Enterobacter amnigenus | 473 | BB5 | no |
| Enterobacter cloacae | 18 | | no |
| Enterobacter asburiae | 16 | | no |
| Enterococcus durans | 879 | | no |
| Escherichia coli | 687 | ECOR 05 | no |
| Escherichia coli | 734 | ECOR 52 | no |
| Klebsiella granulomatis | 75 | KC2668 | no |
| Klebsiella oxytoca | 366 | DSMZ 5175 | no |
| Klebsiella pneumoniae | 207 | DSMZ 30102 | no |
| Kocuria rhizophila | 22 | | no |
| Lactobacillus casei (393) | 356 | 393 | no |
| Lactobacillus casei (862) | 351 | 862 | no |
| Lactobacillus casei (864) | 349 | 864 | no |
| Lactobacillus plant (2410) | 350 | 2410 | no |
| Micrococcus luteus | 24 | | no |
| Pseudomonas fluoreszens | 370 | | no |
| Ralstonia picketti | 420 | | no |
| Salmonella enteritits SZ 15 | 478 | | no |
| Salmonella dublin | 959 | SL 5608 20031113 | no |
| Salmonella berta | 956 | IS 69 20031113 | no |
| Staphylococcus aureus | 456 | | no |
| Staphylococcus aureus | 457 | | no |
| Staphylococcus aureus | 458 | | no | b) LB Test
Examination of the binding of *listeria* to magnetic particles via the fusion proteins:

0.5 ml of a fresh ON culture were added to 2 ml of *listeria* enrichment broth acc. FDA (Profos AG) and cultivated to an $OD_{600}$ of about 1 at 37° C. (corresponds to 0.5 to $1\times10^9$ cfu/ml). The cultures were diluted in PBST to about $1\times10^4$ cfu/ml. 1 µg of STREP-TAG®-HisTag-GFP-CBD511_f3 fusion protein was added to 1 ml of the respective cell dilutions and briefly mixed. After addition of 50 µg MagPrep-Streptavidin (Merck) the mixtures were incubated for 20 min in an overhead rolator at RT. Subsequently, the complexes of magnetic particles, fusion protein and *listeria* were collected in a magnetic field at the vessel wall and the supernatant (SN1) was transferred to a sterile vessel. The particle-protein-listeria-complex was washed in 1 ml of PBST for 10 min in the overhead rolator, collected in a magnetic field at the vessel wall and the supernatant was added to SN1. The complex was resuspended in 1 ml of PBST. Subsequently, serial dilutions in PBST of the combined supernatants and of the resuspended complexes were plated on Oxford agar (Profos AG) and incubated for 24 h at 37° C. The plates were counted and the portion of the *listeria* adhering to the magnetic particles was calculated in percent of the in toto recovered *listeria*.

Table 2 shows the result of the serotype dependency of the binding properties of different cell binding domains from *listeria* endolysins to strains of the genus *listeria*. CBD118 stands for the cell binding domain of the endolysin Ply118; CBD500 stands for the cell binding domain of the endolysin Ply500; CBD511f2 and CBD511_f3 stand for the variants of the cell binding domain of the endolysin Ply511; NC test means: the binding of the respective STREP-TAG®-HisTag-GFP-CBD-fusions were determined via the binding to cells immobilised on nitrocellulose membrane (experiment 2a) and detection over streptaktin-alkaline-phosphatase-conjugate; LB-test means: the binding was determined via the removal of *listeria* from solutions using streptavidin coated magnetic particles and the mono-biotinylated cell binding domain Bio-GFP-CBD511_f3 (experiment 2b).

Table 2 shows the binding of the cell binding domain to *listeria*

| Species | Strain Profos Culture Collection (ProCC) | alternative strain description | Serovar | NC-Test CBD118 | CBD500 | CBD511_f2 | LB-Test CBD511_f3 |
|---|---|---|---|---|---|---|---|
| L. monocytogenes | 992 | SLCC 4955 | 1/2a | yes | no | yes | yes |
| | 993 | SLCC 6204 | 1/2a | (yes) | no | yes | yes |
| | 995 | SLCC 7150 | 1/2a | | | | yes |
| | 1095 | EGDe | 1/2a | yes | no | yes | yes |
| | 996 | SLCC 6031 | 1/2b | no | no | yes | yes |
| | 997 | SLCC 7136 | 1/2b | | | | yes |
| | 998 | SLCC 7151 | 1/2b | yes | no | yes | yes |
| | 999 | SLCC 7152 | 1/2b | (yes) | no | yes | yes |
| | 772 | ATCC 19112 | 1/2c | yes | no | yes | yes |
| | 1000 | SLCC 4950 | 1/2c | yes | no | yes | yes |
| | 1001 | SLCC 6793 | 1/2c | (yes) | no | yes | yes |
| | 1002 | SLCC 7154 | 1/2c | (yes) | no | yes | yes |
| | 1003 | SLCC 7290 | 1/2c | (yes) | no | yes | yes |
| | 1134 | WSLC 1211 | 3a | | | | yes |
| | 1135 | WSLC 1485 | 3a | | | | yes |
| | 1136 | SLCC 1694 | 3b | | | | yes |
| | 1137 | WSLC 1444 | 3b | | | | yes |
| | 1138 | SLCC 2479 | 3c | | | | yes |
| | 1139 | WSLC 1435 | 3c | | | | yes |
| | 1140 | ATCC 19114 | 4a | | | | yes |
| | 1141 | WSLC 1049 | 4a | | | | yes |
| | 775 | ATCC 23074 | 4b | no | yes | yes | yes |
| | 776 | Scott A | 4b | no | yes | yes | yes |
| | 1004 | SLCC 4013 | 4b | no | yes | yes | yes |
| | 1005 | SLCC 7139 | 4b | no | yes | yes | yes |
| | 1006 | SLCC 7194 | 4b | no | yes | yes | yes |
| | 1007 | SLCC 7356 | 4b | no | yes | yes | yes |
| | 1142 | ATCC 19116 | 4c | | | | yes |
| | 1143 | WSLC 1033 | 4d | | | | yes |
| | 1144 | WSLC 1048 | 4d | | | | yes |
| | 1145 | WSLC 1018 | 4e | | | | yes |
| | 1146 | SLCC 2482 | 7 | | | | yes |
| | 774 | WSLC 3008 | ? | no | yes | yes | yes |
| L. innocua | 1147 | WSLC 2011 | 6a | | | | yes |
| | 773 | WSLC 2012 | 6b | no | yes | yes | yes |
| | 1148 | WSLC 2054 | 6b | | | | yes |
| | 1009 | SLCC 7160 | ? | no | yes | yes | yes |
| | 1010 | SLCC 5326 | ? | yes | yes | yes | yes |
| | 1011 | SLCC 7166 | ? | no | yes | yes | yes |
| L. ivanovii | 1012 | SLCC 2098 | ? | no | yes | yes | yes |
| | 1013 | SLCC 2102 | ? | no | yes | yes | yes |
| | 1014 | SLCC 4706 | ? | no | yes | yes | yes |
| | 1015 | SLCC 4121 | ? | yes | yes | yes | yes |
| (ssp. *ivanovii*) | 1149 | WSLC 3010 | 5 | | | | yes |
| (ssp. *ivanovii*) | 1150 | WSLC 30165 | 5 | | | | yes |
| (ssp. *londonensis*) | 1151 | WSLC 3060 | 5 | | | | yes |
| L. seeligeri | 1154 | WSLC 40127 | ? | | | | yes |
| | 1155 | WSLC 40130 | ? | | | | yes |
| | 1156 | WSLC 4453 | 4b | | | | yes |

| Species | Strain Profos Culture Collection (ProCC) | alternative strain description | Serovar | NC-Test CBD118 | CBD500 | CBD511_f2 | LB-Test CBD511_f3 |
|---|---|---|---|---|---|---|---|
| L. welshimeri | 1158 | WSLC 50149 | 1/2b | | | | yes |
| | 1157 | WSLC 50146 | 6a | | | | yes |
| | 1159 | WSLC 50150 | 6b | | | | yes |
| L. grayi (ssp. g | 1160 | WSLC 6036 | | | | | yes |

Experiment 3

Comparison of the Cell Binding Property of the STREP-TAG®-HisTag-CBD511_f3 with STREP-TAG®-HisTag-CBD500

0.5 ml of a fresh ON culture (*L. monocytogenes* ScottA, serovar 4b; *L. monocytogenes* EGDe, serovar 1/2a) were added to 2 ml of *listeria* enrichment broth acc. FDA (Profos AG) and cultivated to an $OD_{600}$ of about 1 at 37° C. (corresponds to 0.5 to $1\times10^9$ cfu/ml). The cultures were diluted in PBST to about $1\times10^4$ cfu/ml. 1 μg, 5 μg and 10 μg of STREP-TAG®-HisTag-GFP-CBD511_f3 fusion protein and STREP-TAG®-HisTag-CBD500 fusion protein, respectively, were added to 1 ml of the respective cell dilutions and briefly mixed. After addition of 50 μg MagPrep-Streptavidin (Merck) the mixtures were incubated for 20 min in an overhead rolator at RT. Subsequently, the complexes of magnetic particles, fusion protein and *listeria* were collected in a magnetic field at the vessel wall and the supernatant (SN1) was transferred to a sterile vessel. The particle-protein-listeria-complex was washed in 1 ml of PBST for 10 min in the overhead rolator, collected in a magnetic field at the vessel wall and the supernatant was added to SN1. The complex was resuspended in 1 ml of PBST. Subsequently, serial dilutions in PBST of the combined supernatants and of the resuspended complexes were plated on Oxford agar (Profos AG) and incubated for 24 h at 37° C. The plates were counted and the portion of the *listeria* adhering to the magnetic particles was calculated in percent of the in toto applied cells.

In contrast to CBD500, *listeria* of the serotype 1/2a could be enriched in a protein concentration dependent manner using CBD511. The serotype 4b is enriched both with the CBD511 and the CBD500 in a protein concentration dependent manner.

Experiment 4

Dependency of the binding of *listeria* to magnetic particles in the 2-step-method on the concentration of biotinylated CBD511 constructs-Bio-OD-CBD511_f3 and Bio-Av-GFP-CBD511_f3.

Either the biotinylation domain of the α subunit of the *Klebsiella pneumoniae* oxalacetate decarboxylase (GenBank Accession No. J03885, U.S. Pat. No. 5,252,466, EP 0511747, Schwarz et al., Journal of Biological Chemistry 263 (1988), 9640-9645) as biotinylation domain or the Avi-Tag (U.S. Pat. No. 5,723,584; U.S. Pat. No. 5,874,239) were N-terminally cloned to the CBD511_f3 using molecular biological standard techniques. Because of the small size of the Avi-Tag GFP was additionally introduced as "linker domain", as depicted in FIG. 1A. The constructs were called Bio-OD-CBD511_f3 and Bio-Av-GFP-CBD511_f3, respectively. The binding tests with Bio-OD-CBD511_f3 (FIG. 4A) and Bio-Av-GFP-CBD511_f3 (FIG. 4B) were performed as follows. 0.5 ml each of a fresh ON culture (*L. monocytogenes* ScottA, serovar 4b) were added to 2 ml of *listeria* enrichment broth acc. FDA (Profos AG) and grown to an $OD_{600}$ of about 1 at 37° C. (corresponds to 0.5 to $1\times10^9$ cfu/ml). The cultures were adjusted to $1\times10^3$ to $1\times10^4$ cfu/ml in PBST (10 mM sodium phosphate pH 8, 150 mM sodium chloride, 0.05% Tween 20) and further serial dilutions were plated on Oxford agar (Profos AG) to determine the actual cell number. Bio-OD-CBD511_f3 was added in the concentrations 0, 0.001, 0.005, 0.01, 0.02, 0.1, 0.3, 0.5, 0.75, 1, 1.5, 2, 3, 4, 5, 10, 20, and 40 μg/ml to 1 ml cell dilution, Bio-Av-GFP-CBD511_f3 in the concentrations 0.5, 1, 2, and 10 μg/ml, briefly shaken and after addition of Streptavidin-magnetic-particles (Roche) to 50 μg/ml the mixtures were incubated for 20 min in an overhead rolator at RT. Subsequently, the particle-listeria-complexes were collected in a magnetic field at the vessel wall, the supernatant was removed and transferred to a sterile 2 ml Eppendorf-cup. The particle-listeria-complex was washed in 1 ml of PBST for 10 min in an overhead relator, collected in a magnetic field at the vessel wall; the supernatant was added to the first supernatant.

The *listeria*-particle-complex was resuspended in 1 ml of PBST. Subsequently, serial dilutions of the combined supernatants and of the resuspended complexes in PBST were plated on Oxford agar (Profos AG) and incubated for 24 h at 37° C. The plates were counted and the portion of *listeria* adhering to the magnetic particles was calculated in percent of the in toto applied cells.

It was shown that using the Bio-OD-CBD_f3 (A) the maximal yield of *listeria* is achieved in the 2-step-method starting from a concentration of 0.3 μg/ml and remains constant over a wide concentration range up to 40 μg/ml, in the case of Bio-Av-GFP-CBD_f3 (B) the maximum yield of bound *listeria* is achieved starting from about 2 μg/ml protein.

Experiment 5

Dependency of the Cell Binding of the 2-Step-Method on pH 0.5 ml of a fresh ON culture (*L. monocytogenes* ScottA, serovar 4b; *L. monocytogenes* EGDe, serovar 1/2a) were added to 2 ml of *listeria* enrichment broth acc. FDA (Profos AG) and grown to an $OD_{600}$ of about 1 at 37° C. (corresponds to 0.5 to $1\times10^9$ cfu/ml). The cultures were diluted in buffer X (10 mM sodium citrate, 10 mM sodium phosphate), adjusted to the respective pH-value, to about $1\times10^4$ cfu/ml. 5 μg of the Bio-Av-GFP-CBD_f3 fusion proteins were added to 1 ml each of the cell dilutions and briefly mixed. After addition of 50 μg MagPrep-Streptavidin (Merck) the mixtures were incubated for 20 min in an overhead rolator at RT. Subsequently, the complexes of magnetic particles, fusion protein and *listeria* were collected in a magnetic field at the vessel wall and the supernatant (SN1) was transferred to a sterile vessel along with a 1/10 volume of 10×PBST. The particle-protein-listeria-complex was washed in 1 ml of buffer X for 10 min in an overhead rolator, collected in a magnetic field at the vessel wall and the supernatant was added to SN1. The complex was resuspended in 1 ml of PBST. Subsequently, serial dilutions of the combined supernatants and of the resuspended complexes in PBST were plated on Oxford agar (Profos AG) and incubated for 24 h at 37° C. The plates were counted and the portion of the *listeria* adhering to the magnetic particles was calculated in percent of the in toto applied cells.

It was shown that the 2-step-method for enrichment of *listeria* of serotype 4b and serotype 1/2a results in consistent yields over the pH range from 5 to 10.

Experiment 6

Dependency of the Cell Binding of the 2-Step-Method on the Salt Content 0.5 ml of a fresh ON culture (*L. monocytogenes* ScottA, serovar 4b; *L. monocytogenes* EGDe, serovar 1/2a) were added to 2 ml of *listeria* enrichment broth acc. FDA (Profos AG) and grown to an $OD_{600}$ of about 1 at 37° C. (corresponds to 0.5 to $1 \times 10^9$ cfu/ml). The cultures were diluted in 10 mM sodium phosphate, pH 8, 0.05% Tween 20 and a salt content of 0, 100, 200, 400, 600, 800, and 1000 mM NaCl to about $1 \times 10^4$ cfu/ml. 5 µg of the STREP-TAG®-HisTag-GFP-CBD511_f3 fusion protein were added to 1 ml each of the cell dilutions and briefly mixed. After addition of 50 µg MagPrep-Streptavidin (Merck) the mixtures were incubated for 20 min in an overhead rolator at RT. Subsequently, the complexes of magnetic particles, fusion protein and *listeria* were collected in a magnetic field at the vessel wall and the supernatant (SN1) was transferred to a sterile vessel. The particle-protein-listeria-complex was washed in 1 ml of PBST for 10 min in an overhead rolator, collected in a magnetic field at the vessel wall and the supernatant was added to SN1. The complex was resuspended in 1 ml of PBST. Subsequently, serial dilutions in PBST of the combined supernatants and of the resuspended complexes were plated on Oxford agar (Profos AG) and incubated for 24 h at 37° C. The plates were counted and the portion of the *listeria* adhering to the magnetic particles was calculated in percent of the in toto applied cells.

Whereas the enrichment efficiency in the case of serotype 1/2 a remains constant almost over the entire range from 0 to 1 M NaCl, it declines in the case of serotype 4b with increasing salt concentration.

Experiment 7

Cell Recovery Using the 1-Step-Method and the 2-Step-Method in Dependency on the Duration of Incubation Covalent coupling of Bio-Av-GFP-CBD_f3 to the magnetic particles DYNABEADS® M-270 Epoxy (Dynal): the DYNABEADS® were resuspended in diglym according to the manufacturer's instructions and washed according to the instructions prior to coupling, equilibrated and taken up in 250 µl of sterile sodium phosphate (0.1 M, pH 7.5). Subsequently, 1 ml of 3 M ammonia sulphate solution in 0.1 M sodium phosphate pH 7.4 and 1 ml protein solution (STREP-TAG®-HisTag-CBD511_f2 in 0.1 M sodium phosphate pH 7.4) were added, mixed and incubated overnight at 4° C. and subsequently for 8 h at RT in a rolator. The magnetic particles were collected in a magnetic field, the supernatant was removed and the magnetic particles were washed 2× in 10 mM sodium phosphate pH 7.5, 150 mM sodium chloride, 0.1% bovine serum albumin and 0.02% sodium azide for 20 min at RT and subsequently stored in this buffer at 4° C. 0.5 ml of a fresh ON culture (*L. monocytogenes* ScottA, serovar 4b; *L. monocytogenes* EGDe, serovar 1/2a) were added to 2 ml of *listeria* enrichment broth acc. FDA (Profos AG) and grown to an $OD_{600}$ of about 1 at 37° C. (corresponds to 0.5 to $1 \times 10^9$ cfu/ml). The cultures were diluted in PBST to about $1 \times 10^4$ cfu/ml.

1-step-method: 300 µg/ml of the Bio-Av-GFP-CBD_f1 coated magnetic particles (DYNABEADS® Epoxy) were added to 1 ml each of the cell dilutions, and the mixtures were incubated for 5, 10, 20, 40, and 60 min in an overhead rolator at RT.

2-step-method: 5 µg of the Bio-Av-GFP-CBD_f3 fusion protein were added to 1 ml each of the cell dilutions and briefly mixed. Subsequently, MagPrep-Streptavidin-particles (Merck) were added to 50 µg/ml, and the mixtures were incubated for 5, 10, 20, 40, and 60 min in an overhead rolator at RT.

Subsequently, the particle-listeria-complexes were collected in a magnetic field at the vessel wall and the supernatant (SN1) was transferred to a sterile vessel. The particle-listeria-complex was washed in 1 ml of PBST for 10 min in an overhead rolator, collected in a magnetic field at the vessel wall and the supernatant was added to SN1. The complex was resuspended in 1 ml of PBST. Subsequently, serial dilutions in PBST of the combined supernatants and the resuspended complexes were plated on Oxford agar (Profos AG) and incubated for 24 h at 37° C. The plates were counted and the portion of the *listeria* adhering to the magnetic particles was calculated in percent of the in toto applied cells.

In case of the 2-step-method the maximal enrichment efficiency is obtained already after an incubation time of 5 min. In case of the 1-step-method the same enrichment efficiency as found with the 2-step-method is obtained after 60 min only.

Experiment 8

Detection of *Listeria* in Camembert Using the 1-Step- and the 2-Step-Method 300 g of Camembert from a supermarket were sterilely divided into 25 g portion units and stored in Stomacher bags at −80° C. One portion unit was examined for presence of *listeria* according to the norm ISO: 11290-1:1996 FDAM 1. In the case of absence of a *listeria* contamination 5 portion units were thawed at RT and infected with different amounts of *L. monocytogenes* ScottA. For this purpose an ON culture was diluted 1/5 and incubated to an $OD_{600}$ of about 1 at 37° C. Subsequently, serial dilutions were performed in sterile PBST. Under the assumption of 0.5 to $1 \times 10^9$ cfu/ml at $OD_{600}$ of 1 the portion units were contaminated with 0, 1-10, 11-50, 50-100, and 100-500 cfu/25 g Camembert and stored ON at 4° C. For the exact determination of the cell numbers duplicates of the dilutions were plated on Oxford agar (Profos AG), the plates were incubated for 24 h at 37° C. and counted. 225 ml Fraser ½ medium (Profos AG) were sterilely added to the portion units, homogenised for 1 min in a Stomacher and incubated at 30° C. After an incubation time of 4 h, 6 h, and 24 h 1 ml was removed per mixture.

1-step-method: 300 µg/ml of the STREP-TAG®-HisTag-CBD511_f2 coated magnetic particles (DYNABEADS® Epoxy) were added to 1 ml homogenate, and the mixture was incubated for 20 min in an overhead rolator at RT.

2-step-method: 5 µg of the StrepTag-HisTag-GFP-CBD511_f3 fusion protein were added to 1 ml homogenate and briefly mixed. Subsequently, MagPrep-Streptavidin-particles (Merck) were added to 50 µg/ml, and the mixtures were incubated for 20 min in an overhead rolator at RT.

Subsequently, the particle-listeria-complexes were collected in a magnetic field at the vessel wall and the supernatant was removed. The particle-listeria-complex was washed 3× with 1 ml of PBST for 10 min in an overhead rolator, collected in a magnetic field at the vessel wall and the supernatant was discarded each time. The particle-listeria-complexes were resuspended in 100 µl of PBST and plated on Oxford agar (Profos AG). After 24 h and 48 h at 37° C. the plates were counted and the portion of *listeria* adhering to the magnetic particles was calculated in percent of the in toto applied cells. In parallel, the contaminated mixtures were examined according to norm ISO: 11290-1:1996 FDAM 1 for *listeria*. For this purpose, 100 µl were added to 10 ml Fraser medium (Profos AG) at the indicated time points, incubated for 24 h at 37° C. in a roler and subsequently plated on Oxford agar (Profos AG). All mixtures were performed in quadruplets.

It was shown that both using the 1-step-method and the 2-step-method the necessary enrichment times are significantly shorter than using the method according to ISO: 11290-1: 1996, in order to detect minor *listeria* contaminations in Camembert. Concerning the reduction of the enrichment time the results for the 2-step-method are better than for the 1-step-method.

Experiment 9

Detection of *Listeria* in Raw Ham and in Shrimps According to the 1 ml- and the 10 ml-2-Step-Method 300 g raw ham and 300 g shrimps from a supermarket were divided sterilely in 25 g portion units and stored in Stomacher bags at −80° C. One portion unit each was examined for the presence of *listeria* according to the norm ISO: 11290-1:1996 FDAM 1. In case of absence of a *listeria* contamination 5 portion units were thawed at RT and infected with different amounts of *L. monocytogenes* ScottA. For this purpose, an ON culture was diluted ⅕ and incubated to an $OD_{600}$ of about 1 at 37° C. Subsequently, serial dilutions were performed in sterile PBST. Under the assumption of 0.5 to $1\times10^9$ cfu/ml at an $OD_{600}$ of 1 the portion units were contaminated with 0, 1-10, 11-50, 50-100, and 100-500 cfu/25 g food and stored ON at 4° C. For the exact determination of the cell numbers duplicates of the dilutions were plated on Oxford agar (Profos AG), the plates were incubated for 24 h at 37° C. and counted.

225 ml Fraser ½ medium (Profos AG) were added sterilely to the portion units, homogenised for 1 min in a Stomacher and incubated at 30° C. After an incubation time of 4 h and 6 h 2×1 ml and 2×10 ml were taken per portion unit. 2.5 µg/ml of STREP-TAG®-HisTag-GFP-CBD511_f3 fusion protein were added to the homogenate and briefly vortexed. Subsequently, MagPrep-Steptavidin-particles (Merck) were added to 100 µg/ml in a 1 ml mixture and to 50 µg/ml in a 10 ml mixture, and the mixtures were incubated for 20 min in an overhead rolator at RT. The particle-listeria-complexes were collected in a magnetic field at the vessel wall and the supernatant was removed. The particle-listeria-complex was washed 2× with 1 ml of PBST by pipetting it up and down several times and resuspended in 100 µl of PBST and plated on Oxford agar (Profos AG). After 24 h and 48 h at 37° C. the plates were counted and the portion of *listeria* adhering to the magnetic particles calculated in percent of the in toto applied cells. In parallel, the contaminated mixtures were examined for *listeria* according to the norm ISO: 11290-1:1996 FDAM 1. For this purpose, 100 µl were added to 10 ml Fraser medium (Profos AG) at the indicated time points, incubated for 24 h at 37° C. in a roller and subsequently plated on Oxford agar (Profos AG). All mixtures were performed in duplicates.

It became apparent that *listeria* in ham and shrimps can be detected faster by enrichment using the 2-step-method than using the method according to ISO: 11290-1:1996. A further reduction of the enrichment time may be accomplished using the 10 ml-2-step-method.

Experiment 10

Detaching the *listeria* from the Magnet Particles 0.5 ml of a fresh ON culture of *L. monocytogenes* ScottA were added to 2 ml of *listeria* enrichment broth acc. FDA (Profos AG) and grown to an $OD_{600}$ of about 1 at 37° C. (corresponds to about 0.5 to $1\times10^9$ cfu/ml). The cultures were diluted in PBST to about $1\times10^4$ cfu/ml.

1 µg/ml StepTag-HisTag-GFP-CBD511_f3 fusion protein was added to 0.5 ml each of the cell dilutions and briefly mixed. After addition of 50 µg/ml MagPrep-Streptavidin (Merck) the mixtures were incubated for 20 min in an overhead rolator at RT. Subsequently, the complexes of magnetic particles, fusion protein and *listeria* were collected in a magnetic field at the vessel wall and the supernatant (SN1) was transferred to a sterile vessel. The particle-protein-listeria-complex was washed in 1 ml of PBST for 10 min in an overhead rolator, collected in a magnetic field at the vessel wall and the supernatant was added to SN1.

Half of the mixtures were resuspended in 100 µl of PBST, the other half was resuspended in 100 µl of 50 mM sodium phosphate pH 11. After 5 min at RT the magnetic particles were removed and the supernatants were added to 400 µl of PBST. The magnetic particles were resuspended in 0.5 ml.

Serial dilutions with PBST of the supernatants and the resuspended magnetic particles were plated on Oxford agar (Profos AG) and incubated for 24 h at 37° C. The plates were counted and the portion of the *listeria* adhering to the magnetic particles was calculated in percent of the in toto recovered *listeria*.

90% of the *listeria* which were bound to the magnetic particles via the cell binding domain were detached with the pH 11 buffer.

Experiment 11

Enrichment of *Listeria* and Detection Via PCR 0.5 ml of a fresh ON culture of *L. monocytogenes* ScottA were added to 2 ml of *listeria* enrichment broth acc. FDA (Profos AG) and grown to an $OD_{600}$ of about 1 at 37° C. (corresponds to about 0.5 to $1\times10^9$ cfu/ml). The culture was diluted in *listeria* enrichment broth acc. FDA (Profos AG) to about $1\times10^6$ and $1\times10^5$ cfu/ml.

For each cell dilution in *listeria* enrichment broth acc. FDA (Profos AG) 14 mixtures a 1 ml were prepared. 4 mixtures of them were centrifuged (for 5 min at 13,000 rpm in a table top centrifuge), the supernatants were discarded, the cells washed 1× in PBST and pelleted. The cell pellets were stored on ice until further processing.

The cells were isolated from 10 mixtures using the 2-step-method: 20 µg of the STREP-TAG®-HisTag-GFP-CBD511_f2 fusion protein were added to 1 ml each of the cell dilutions and briefly mixed. Subsequently, streptavidin-magnetic-particles (Roche) were added to 100 µg/ml, and the mixtures were incubated for 20 min in an overhead rolator at RT. Subsequently, the particle-listeria-complexes were collected in a magnetic field at the vessel wall, the supernatant was removed and discarded. The particle-listeria-complex was washed in 1 ml of PBST for 10 min in an overhead rolator, collected in a magnetic field at the vessel wall; the supernatant was discarded.

The particle-listeria-complex of 2 mixtures was resuspended in 1 ml of PBST. Serial dilutions thereof were plated on Oxford agar (Profos AG) and incubated for 24 h at 37° C. In addition, serial dilutions of the starting cell dilutions having estimated $10^6$ and $10^5$ cfu/ml were plated on Oxford agar (Profos AG) and incubated for 24 h at 37° C. The plates were counted and the actual cell number ($1.4 \times 10^5$ and $1.4 \times 10^6$ cfu/ml) and the portion of the *listeria* adhering to the magnetic particles were calculated in percent of the in toto applied cells (85-95%).

The particle-listeria-complex of 4 mixtures was resuspended in 20 µl of 150 mM sodium phosphate pH 11, incubated for 15 min at RT; subsequently the magnetic particles were collected in a magnetic field at the vessel wall and the supernatant was added quantitatively to 10 µl of 150 mM sodium phosphate pH 6 (mixtures A). The particle-listeria-complex of the 4 remaining mixtures was resuspended in 20 µl of PBST (mixtures B). Each of the 4 mixtures of the centrifuged cells was also resuspended in 20 µl of PBST (mixtures C).

10 µl of PBST were added to 2 mixtures of A, B, and C each; to each of the remaining 2 mixtures 10 µl of PBST with Ply511 (2 µg/ml) were added and incubated at 40° C. for 5-10 min. Subsequently, 5 µl of proteinase K (1 mg/ml PBST) were added to all 4 mixtures, incubated for 5 min at 56° C. and then for 5 min at 94° C. The magnetic particles of the mixtures B were removed in a magnetic field and 5 µl of all mixtures A, B, and C were used in a PCR reaction according to Aznar & Alarcon (Aznar R & Alarcon B (2002): On the specificity of PCR detection of *Listeria monocytogenes* in food, System. Appl. Microbiol. 25, 109-119), and subsequently the reaction products were separated using a 1% agarose gel.

It could be shown that in all 3 cases (centrifugation, 2-step-method with cracking at the magnetic particles and 2-step-method with detaching from the magnetic particles) the addition of endolysin Ply511 to the cracked cells significantly improves the sensitivity of the detection. Whereas with the lysis of the *listeria* at the magnetic particles the same sensitivity is obtained as in the case when the cells are centrifuged, the signal strength in the PCR is weaker if the cells are detached from the magnetic particles prior to cracking using a pH 11 buffer.

Experiment 12

Detection of *listeria* in Frankfurter Sausages and Mozzarella 225 ml FDA medium were each added to 25 g Frankfurter and mozzarella, respectively and the portions were sterilely homogenised in Stomacher bags. The samples were incubated overnight at 30° C. Prior to the *listeria* detection the samples were buffered each with 1/10 volume of PBST.

1-step-method: 300 µg/ml of the magnetic particles (DYNABEADS® M270 Epoxy) coated with Bio-Av-GFP-CBD511_f3 were added to 1 ml homogenate, and the mixture was incubated for 20 min in an overhead rolator at RT.

2-step-method: 0.5, 2, 5, or 10 µg of the Bio-Av-GFP-CBD511_f3 fusion protein were each added to 1 ml homogenate and briefly mixed. Subsequently, MagPrep-Streptavidin-particles (Merck) were added to 50 µg/ml, and the mixtures were incubated for 20 min in an overhead rolator at RT.

Subsequently, the particle-listeria-complexes were collected in a magnetic field at the vessel wall and the supernatant was removed. The particle-listeria-complex was washed 1× with 1 ml of PBST for 10 min in an overhead rolator, collected in a magnetic field at the vessel wall and the supernatant was discarded in each case. The particle-listeria-complexes were resuspended in 100 µl of PBST and plated on Oxford agar (Profos AG). After 24 h at 37° C. the plates were counted and the portion of *listeria* adhering to the magnetic particles were calculated in percent of the in toto applied cells. All mixtures were performed twofold.

It was shown that both from Frankfurter sausages and also from mozzarella *listeria* could be isolated with the help of the Bio-Av-GFP-CBD511_f3 fusion protein. In the case of mozzarella this was achieved with the strain EGDe significantly better than with ScottA. Slightly higher concentrations of protein are used with food in order to achieve a high binding efficiency. Whereas the 1-step-method in the case of Frankfurter sausages and the strain EGDe exhibits a high binding efficiency, under all other conditions the 2-step-method is suited better.

The invention claimed is:

1. A polypeptide that binds *Listeria*, but does not exhibit any cell wall hydrolysing enzymatic activity, wherein the polypeptide comprises an endolysin Ply511 fragment including SEQ ID NO: 2 residues 180-341, but no contains more of SEQ ID NO: 2 than residues 116-341.

2. The polypeptide according to claim 1, comprising an amino acid sequence according to SEQ ID NO:4, 6, or 8.

3. The polypeptide according to claim 1, wherein the polypeptide fragment further comprises an affinity tag or a spacer molecule.

4. The polypeptide according to claim 3, wherein the affinity tag is a His-Tag, Trp-Ser-His-Pro-Gly-Phe-Lys (SEQ ID NO:9), Avi-Tag, or a biotinylation domain.

5. The polypeptide according to claim 3, wherein the spacer molecule is green fluorescent protein, maltose binding protein or a biotinylation domain.

6. A nucleic acid molecule comprising a sequence coding for a polypeptide fragment according to claim 1.

7. The acid molecule according to claim 6, comprising a sequence according to SEQ ID NO:3, 5, or 7.

8. A method for enrichment and/or removal of *Listeria* from a sample-comprising the steps of:
  a) incubating or contacting a sample with a polypeptide according to claim 1, which is unspecifically or directedly immobilised to a solid carrier, and
  b) separating the carrier-polypeptide *Listeria*-complex from the sample.

9. The method according to claim 8, further comprising after step b) the step of:
  c) washing away of sample components unspecifically adhering to the carrier-polypeptide *Listeria*-complex.

10. The method according to claim 8, wherein the steps a) and b) are performed in a chromatography column flow through method.

11. The method according to claim 8, wherein the solid carrier is cellulose, filtration media, glass particles, magnet particles, centrifugation-materials, sedimentation-materials or filling materials for chromatography columns.

12. A method for the enrichment and/or removal of *Listeria* from a sample comprising the steps of:
  a) incubating or contacting a sample with a polypeptide according to claim 3,
  b) contacting and incubating of *Listeria*-polypeptide-complex with a carrier, which is coated with the respective binding partner of the polypeptide or the affinity tag, and
  c) separating the carrier-polypeptide *Listeria*-complex from the sample.

13. The method according to claim 12, further comprising after step c) the step of:
  d) washing away of sample components unspecifically adhering to the carrier-polypeptide *Listeria*-complex.

14. The method according to claim 8, further comprising after step b) a step of detecting the *Listeria*.

15. A kit comprising (i) a carrier onto which a polypeptide fragment according to claim 1 is immobilised, and (ii) washing buffer, detaching buffer and/or cell cracking buffer.

16. A kit comprising (i) a polypeptide fragment according to claim 3, (ii) a carrier coated with the respective binding partner of the affinity tag or the spacer molecule, and (iii) washing buffer, detaching buffer and/or cell cracking buffer.

17. The method according to claim 12, further comprising after step c) a step of detecting the *Listeria*.

18. The polypeptide fragment of claim 1, wherein the polypeptide comprises the amino acid sequence of residues 116-341 of SEQ ID NO: 2.

19. The polypeptide fragment of claim 3, wherein the spacer molecule comprises an affinity tag or a biotin.

* * * * *

UNITED STATES PATENT AND TRADEMARK OFFICE
CERTIFICATE OF CORRECTION

| | | |
|---|---|---|
| PATENT NO. | : 8,350,005 B2 | Page 1 of 1 |
| APPLICATION NO. | : 12/064317 | |
| DATED | : January 8, 2013 | |
| INVENTOR(S) | : Michael Schutz et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 540 days.

Signed and Sealed this
Fifteenth Day of July, 2014

Michelle K. Lee
*Deputy Director of the United States Patent and Trademark Office*

SEQUENCE LISTING

```
<160> NUMBER OF SEQ ID NOS: 9

<210> SEQ ID NO 1
<211> LENGTH: 1026
<212> TYPE: DNA
<213> ORGANISM: Artificial
<220> FEATURE:
<223> OTHER INFORMATION: A511 Endolysin Ply511 bacteriophage

<400> SEQUENCE: 1
atggtaaaat ataccgtaga gaacaaaatt attgcaggat tacctaaagg taaactaaaa      60
ggggctaact ttgttattgc tcatgaaact gcaaatagca agtctactat tgacaatgaa     120
gtaagctaca tgactaggaa ctggaagaac gcatttgtaa ctcactttgt aggtggcgga     180
ggtagagtcg ttcaggttgc taatgtaaac tatgtttctt ggggagcagg tcagtatgct     240
aactcttatt cctatgcgca ggtagagttg tgccgtacaa gtaatgcaac tacatttaag     300
```

-continued

```
aaagactatg aagtgtactg tcaattacta gtagacctag ctaaaaaagc aggtatccct    360
attacacttg actctggtag taaaactagt gataaaggta ttaaatccca taaatgggtt    420
gctgataagc taggaggaac aacacaccaa gacccatatg cttacttaag ctcatggggt    480
attagtaaag cacaatttgc tagtgacttg gctaaagtat ctggcggagg aaacacagga    540
acagcgccag ctaaaccaag cacaccagca cctaaaccaa gcacaccatc tactaaccta    600
gacaaacttg gcttagtaga ctacatgaac gctaagaaaa tggactctag ctacagtaac    660
agagataagt tagctaaaca gtatggtatt gctaactatt caggaacagc tagccagaac    720
actacactcc ttagtaaaat taaggagga gcacctaaac caagcacacc agcacctaaa    780
cctagtacat ctacagctaa gaaaatttat ttcccaccaa ataaggaaa ctggtctgtg    840 tatccaacaa ataaagcacc cgttaaggct aatgctattg gtgctattaa ccctactaaa    900
ttcggaggat tgacttacac tatccaaaaa gatagaggaa acggtgtata cgaaatccaa    960
acagaccaat tcggcagagt tcaagtctat ggtgcaccta gtacaggagc agttatcaaa    1020
aaataa                                                              1026
```

<210> SEQ ID NO 2
<211> LENGTH: 341
<212> TYPE: PRT
<213> ORGANISM: Artificial
<220> FEATURE:
<223> OTHER INFORMATION: A511 Endolysin Ply511 bacteriophage

<400> SEQUENCE: 2

```
Met Val Lys Tyr Thr Val Glu Asn Lys Ile Ile Ala Gly Leu Pro Lys
1               5                   10                  15

Gly Lys Leu Lys Gly Ala Asn Phe Val Ile Ala His Glu Thr Ala Asn
            20                  25                  30

Ser Lys Ser Thr Ile Asp Asn Glu Val Ser Tyr Met Thr Arg Asn Trp
        35                  40                  45

Lys Asn Ala Phe Val Thr His Phe Val Gly Gly Gly Arg Val Val
    50                  55                  60

Gln Val Ala Asn Val Asn Tyr Val Ser Trp Gly Ala Gly Gln Tyr Ala
65                  70                  75                  80

Asn Ser Tyr Ser Tyr Ala Gln Val Glu Leu Cys Arg Thr Ser Asn Ala
                85                  90                  95

Thr Thr Phe Lys Lys Asp Tyr Glu Val Tyr Cys Gln Leu Leu Val Asp
            100                 105                 110

Leu Ala Lys Lys Ala Gly Ile Pro Ile Thr Leu Asp Ser Gly Ser Lys
        115                 120                 125

Thr Ser Asp Lys Gly Ile Lys Ser His Lys Trp Val Ala Asp Lys Leu
    130                 135                 140

Gly Gly Thr Thr His Gln Asp Pro Tyr Ala Tyr Leu Ser Ser Trp Gly
145                 150                 155                 160

Ile Ser Lys Ala Gln Phe Ala Ser Asp Leu Ala Lys Val Ser Gly Gly
                165                 170                 175

Gly Asn Thr Gly Thr Ala Pro Ala Lys Pro Ser Thr Pro Ala Pro Lys
            180                 185                 190

Pro Ser Thr Pro Ser Thr Asn Leu Asp Lys Leu Gly Leu Val Asp Tyr
        195                 200                 205

Met Asn Ala Lys Lys Met Asp Ser Ser Tyr Ser Asn Arg Asp Lys Leu
    210                 215                 220

Ala Lys Gln Tyr Gly Ile Ala Asn Tyr Ser Gly Thr Ala Ser Gln Asn
225                 230                 235                 240
```

```
Thr Thr Leu Leu Ser Lys Ile Lys Gly Gly Ala Pro Lys Pro Ser Thr
            245                 250                 255

Pro Ala Pro Lys Pro Ser Thr Ser Thr Ala Lys Lys Ile Tyr Phe Pro
        260                 265                 270

Pro Asn Lys Gly Asn Trp Ser Val Tyr Pro Thr Asn Lys Ala Pro Val
    275                 280                 285

Lys Ala Asn Ala Ile Gly Ala Ile Asn Pro Thr Lys Phe Gly Gly Leu
290                 295                 300

Thr Tyr Thr Ile Gln Lys Asp Arg Gly Asn Gly Val Tyr Glu Ile Gln
305                 310                 315                 320

Thr Asp Gln Phe Gly Arg Val Gln Val Tyr Gly Ala Pro Ser Thr Gly
                325                 330                 335

Ala Val Ile Lys Lys
            340

<210> SEQ ID NO 3
<211> LENGTH: 681
<212> TYPE: DNA
<213> ORGANISM: Artificial
<220> FEATURE:
<223> OTHER INFORMATION: A511 Endolysin Ply511 bacteriophage

<400> SEQUENCE: 3
aaagcaggta tccctattac acttgactct ggtagtaaaa ctagtgataa aggtattaaa      60
tcccataaat gggttgctga taagctagga ggaacaacac accaagaccc atatgcttac     120
ttaagctcat ggggtattag taaagcacaa tttgctagtg acttggctaa agtatctggc     180
ggaggaaaca caggaacagc gccagctaaa ccaagcacac cagcacctaa accaagcaca     240
ccatctacta acctagacaa acttggctta gtagactaca tgaacgctaa gaaaatggac     300
tctagctaca gtaacagaga taagttagct aaacagtatg gtattgctaa ctattcagga     360
acagctagcc agaacactac actccttagt aaaattaaag gaggagcacc taaaccaagc     420
acaccagcac taaacctag tacatctaca gctaagaaaa tttatttccc accaaataaa      480
ggaaactggt ctgtgtatcc aacaaataaa gcacccgtta aggctaatgc tattggtgct     540
attaacccta ctaaattcgg aggattgact tacactatcc aaaaagatag aggaaacggt     600
gtatacgaaa tccaaacaga ccaattcggc agagttcaag tctatggtgc acctagtaca     660
ggagcagtta tcaaaaaata a                                                681

<210> SEQ ID NO 4
<211> LENGTH: 226
<212> TYPE: PRT
<213> ORGANISM: Artificial
<220> FEATURE:
<223> OTHER INFORMATION: A511 Endolysin Ply511 bacteriophage

<400> SEQUENCE: 4

Lys Ala Gly Ile Pro Ile Thr Leu Asp Ser Gly Ser Lys Thr Ser Asp
1               5                   10                  15

Lys Gly Ile Lys Ser His Lys Trp Val Ala Asp Lys Leu Gly Gly Thr
            20                  25                  30

Thr His Gln Asp Pro Tyr Ala Tyr Leu Ser Ser Trp Gly Ile Ser Lys
        35                  40                  45

Ala Gln Phe Ala Ser Asp Leu Ala Lys Val Ser Gly Gly Asn Thr
    50                  55                  60

Gly Thr Ala Pro Ala Lys Pro Ser Thr Pro Ala Pro Lys Pro Ser Thr
65                  70                  75                  80
```

Pro Ser Thr Asn Leu Asp Lys Leu Gly Leu Val Asp Tyr Met Asn Ala
            85                  90                  95

Lys Lys Met Asp Ser Ser Tyr Ser Asn Arg Asp Lys Leu Ala Lys Gln
            100                 105                 110

Tyr Gly Ile Ala Asn Tyr Ser Gly Thr Ala Ser Gln Asn Thr Thr Leu
            115                 120                 125

Leu Ser Lys Ile Lys Gly Gly Ala Pro Lys Pro Ser Thr Pro Ala Pro
    130                 135                 140

Lys Pro Ser Thr Ser Thr Ala Lys Lys Ile Tyr Phe Pro Pro Asn Lys
145                 150                 155                 160

Gly Asn Trp Ser Val Tyr Pro Thr Asn Lys Ala Pro Val Lys Ala Asn
                165                 170                 175

Ala Ile Gly Ala Ile Asn Pro Thr Lys Phe Gly Gly Leu Thr Tyr Thr
            180                 185                 190

Ile Gln Lys Asp Arg Gly Asn Gly Val Tyr Glu Ile Gln Thr Asp Gln
            195                 200                 205

Phe Gly Arg Val Gln Val Tyr Gly Ala Pro Ser Thr Gly Ala Val Ile
    210                 215                 220

Lys Lys
225

<210> SEQ ID NO 5
<211> LENGTH: 594
<212> TYPE: DNA
<213> ORGANISM: Artificial
<220> FEATURE:
<223> OTHER INFORMATION: A511 Endolysin Ply511 bacteriophage

<400> SEQUENCE: 5
ggaggaacaa cacaccaaga cccatatgct tacttaagct catggggtat tagtaaagca     60
caatttgcta gtgacttggc taaagtatct ggcggaggaa acacaggaac agcgccagct    120
aaaccaagca caccagcacc taaaccaagc acaccatcta ctaacctaga caaacttggc    180
ttagtagact acatgaacgc taagaaaatg gactctagct acagtaacag agataagtta    240
gctaaacagt atggtattgc taactattca ggaacagcta gccagaacac tacactcctt    300
agtaaaatta aggaggagc acctaaacca agcacaccag cacctaaacc tagtacatct    360
acagctaaga aaatttattt cccaccaaat aaaggaaact ggtctgtgta tccaacaaat    420
aaagcacccg ttaaggctaa tgctattggt gctattaacc ctactaaatt cggaggattg    480
acttacacta tccaaaaaga tagaggaaac ggtgtatacg aaatccaaac agaccaattc    540
ggcagagttc aagtctatgg tgcacctagt acaggagcag ttatcaaaaa ataa         594

<210> SEQ ID NO 6
<211> LENGTH: 197
<212> TYPE: PRT
<213> ORGANISM: Artificial
<220> FEATURE:
<223> OTHER INFORMATION: A511 Endolysin Ply511 bacteriophage

<400> SEQUENCE: 6

Gly Gly Thr Thr His Gln Asp Pro Tyr Ala Tyr Leu Ser Ser Trp Gly
1               5                   10                  15

Ile Ser Lys Ala Gln Phe Ala Ser Asp Leu Ala Lys Val Ser Gly Gly
            20                  25                  30

Gly Asn Thr Gly Thr Ala Pro Ala Lys Pro Ser Thr Pro Ala Pro Lys
        35                  40                  45

```
Pro Ser Thr Pro Ser Thr Asn Leu Asp Lys Leu Gly Leu Val Asp Tyr
    50                  55                  60

Met Asn Ala Lys Lys Met Asp Ser Ser Tyr Ser Asn Arg Asp Lys Leu
65                  70                  75                  80

Ala Lys Gln Tyr Gly Ile Ala Asn Tyr Ser Gly Thr Ala Ser Gln Asn
                85                  90                  95

Thr Thr Leu Leu Ser Lys Ile Lys Gly Gly Ala Pro Lys Pro Ser Thr
            100                 105                 110

Pro Ala Pro Lys Pro Ser Thr Ser Thr Ala Lys Lys Ile Tyr Phe Pro
        115                 120                 125

Pro Asn Lys Gly Asn Trp Ser Val Tyr Pro Thr Asn Lys Ala Pro Val
    130                 135                 140

Lys Ala Asn Ala Ile Gly Ala Ile Asn Pro Thr Lys Phe Gly Gly Leu
145                 150                 155                 160

Thr Tyr Thr Ile Gln Lys Asp Arg Gly Asn Gly Val Tyr Glu Ile Gln
                165                 170                 175

Thr Asp Gln Phe Gly Arg Val Gln Val Tyr Gly Ala Pro Ser Thr Gly
            180                 185                 190

Ala Val Ile Lys Lys
            195

<210> SEQ ID NO 7
<211> LENGTH: 528
<212> TYPE: DNA
<213> ORGANISM: Artificial
<220> FEATURE:
<223> OTHER INFORMATION: A511 Endolysin Ply511 bacteriophage

<400> SEQUENCE: 7
gctagtgact tggctaaagt atctggcgga ggaaacacag gaacagcgcc agctaaacca    60
agcacaccag cacctaaacc aagcacacca tctactaacc tagacaaact tggcttagta   120
gactacatga acgctaagaa aatggactct agctacagta cagagataa gttagctaaa    180 cagtatggta ttgctaacta ttcaggaaca gctagccaga acactacact ccttagtaaa   240
attaaaggag gagcacctaa accaagcaca ccagcaccta aacctagtac atctacagct   300
aagaaaattt atttcccacc aaataaagga aactggtctg tgtatccaac aaataaagca   360
cccgttaagg ctaatgctat tggtgctatt aaccctacta aattcggagg attgacttac   420
actatccaaa aagatagagg aaacggtgta tacgaaatcc aaacagacca attcggcaga   480
gttcaagtct atggtgcacc tagtacagga gcagttatca aaaaataa                528

<210> SEQ ID NO 8
<211> LENGTH: 175
<212> TYPE: PRT
<213> ORGANISM: Artificial
<220> FEATURE:
<223> OTHER INFORMATION: A511 Endolysin Ply511 bacteriophage

<400> SEQUENCE: 8

Ala Ser Asp Leu Ala Lys Val Ser Gly Gly Asn Thr Gly Thr Ala
1               5                   10                  15

Pro Ala Lys Pro Ser Thr Pro Ala Pro Lys Pro Ser Thr Pro Ser Thr
                20                  25                  30

Asn Leu Asp Lys Leu Gly Leu Val Asp Tyr Met Asn Ala Lys Lys Met
            35                  40                  45

Asp Ser Ser Tyr Ser Asn Arg Asp Lys Leu Ala Lys Gln Tyr Gly Ile
    50                  55                  60
```

```
Ala Asn Tyr Ser Gly Thr Ala Ser Gln Asn Thr Thr Leu Leu Ser Lys
 65                  70                  75                  80

Ile Lys Gly Gly Ala Pro Lys Pro Ser Thr Pro Ala Pro Lys Pro Ser
                 85                  90                  95

Thr Ser Thr Ala Lys Lys Ile Tyr Phe Pro Pro Asn Lys Gly Asn Trp
            100                 105                 110

Ser Val Tyr Pro Thr Asn Lys Ala Pro Val Lys Ala Asn Ala Ile Gly
        115                 120                 125

Ala Ile Asn Pro Thr Lys Phe Gly Gly Leu Thr Tyr Thr Ile Gln Lys
        130             135                 140

Asp Arg Gly Asn Gly Val Tyr Glu Ile Gln Thr Asp Gln Phe Gly Arg
145             150                 155                 160

Val Gln Val Tyr Gly Ala Pro Ser Thr Gly Ala Val Ile Lys Lys
                165                 170                 175

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

Trp Ser His Pro Gly Phe Lys
1               5
```